(12) United States Patent
Cottone et al.

(10) Patent No.: US 10,737,075 B2
(45) Date of Patent: Aug. 11, 2020

(54) DRUG ELUTING BALLOON

(71) Applicant: ORBUSNEICH MEDICAL PTE. LTD., Singapore (SG)

(72) Inventors: Robert J. Cottone, Davie, FL (US); Stephen Rowland, Palmetto Bay, FL (US)

(73) Assignee: OrbusNeich Medical PTE. LTD., Singapore (SG)

( * ) Notice: Subject to any disclaimer, the term of this patent is extended or adjusted under 35 U.S.C. 154(b) by 0 days.

(21) Appl. No.: 16/399,248

(22) Filed: Apr. 30, 2019

(65) Prior Publication Data

US 2019/0255300 A1     Aug. 22, 2019

Related U.S. Application Data

(63) Continuation of application No. 16/058,528, filed on Aug. 8, 2018, which is a continuation-in-part of (Continued)

(51) Int. Cl.
    *A61M 25/10*     (2013.01)
    *A61L 29/16*     (2006.01)
    (Continued)

(52) U.S. Cl.
    CPC ......... *A61M 25/104* (2013.01); *A61L 29/145* (2013.01); *A61L 29/146* (2013.01); (Continued)

(58) Field of Classification Search
    CPC .............. A61M 25/10; A61M 25/1027; A61M 25/1002; A61M 25/104; A61M 2025/105; (Continued)

(56) References Cited

U.S. PATENT DOCUMENTS 3,915,921 A    10/1975   Schlatzer, Jr.
4,509,949 A    4/1985   Huang et al.
(Continued)

FOREIGN PATENT DOCUMENTS

AU    2015258300    12/2015
CN    102824198    12/2012
(Continued)

OTHER PUBLICATIONS

Daniel B. Fram, et al. "Localized Intramural Drug Delivery" Interventional Cardiology, JACC vol. 23, No. 7, Jun. 1994, 1470-7; 8 pages.
(Continued)

*Primary Examiner* — Kevin C Sirmons
*Assistant Examiner* — Tezita Z Watts
(74) *Attorney, Agent, or Firm* — Leason Ellis LLP

(57) ABSTRACT

The present invention is an inflatable balloon which is enclosed by an expandable cover which becomes increasingly porous/permeable during expansion. The balloon is coated or enclosed with a matrix which contains a pharmaceutically active agent. During expansion of the balloon, the pharmaceutically active agent is released or extruded through the expandable cover into a body cavity such as an artery or vein. The present invention also provides for a method of treating a disease or condition by delivering the inflatable balloon to a particular body cavity.

26 Claims, 11 Drawing Sheets

Related U.S. Application Data application No. PCT/US2017/016981, filed on Feb. 8, 2017.

(60) Provisional application No. 62/713,881, filed on Aug. 2, 2018, provisional application No. 62/292,557, filed on Feb. 8, 2016.

(51) Int. Cl.
*A61L 31/16* (2006.01)
*A61L 29/14* (2006.01)
*A61F 2/958* (2013.01)
*A61F 2/06* (2013.01)

(52) U.S. Cl.
CPC ......... *A61L 29/16* (2013.01); *A61M 25/1002* (2013.01); *A61F 2/06* (2013.01); *A61F 2/958* (2013.01); *A61F 2250/0067* (2013.01); *A61L 31/16* (2013.01); *A61L 2300/416* (2013.01); *A61L 2300/62* (2013.01); *A61L 2300/624* (2013.01); *A61L 2300/626* (2013.01); *A61L 2300/802* (2013.01); *A61M 2025/1004* (2013.01); *A61M 2025/105* (2013.01); *A61M 2025/1075* (2013.01)

(58) Field of Classification Search
CPC ...... A61M 2025/1004; A61B 17/12136; A61F 2/958; A61F 2/06; A61L 31/16
See application file for complete search history.

(56) References Cited

U.S. PATENT DOCUMENTS

| | | | |
|---|---|---|---|
| 5,102,402 A | 4/1992 | Dror et al. | |
| 5,213,576 A | 5/1993 | Abiuso et al. | |
| 5,269,755 A | 12/1993 | Bodicky | |
| 5,350,361 A | 9/1994 | Tsukashima et al. | |
| 5,370,614 A * | 12/1994 | Amundson | A61F 2/958 604/103.02 |
| 5,653,689 A * | 8/1997 | Buelna | A61F 2/958 604/103.09 |
| 5,700,286 A | 12/1997 | Tartaglia et al. | |
| 5,957,974 A | 9/1999 | Thompson et al. | |
| 6,132,765 A | 10/2000 | DiCosmo et al. | |
| 6,168,617 B1 | 1/2001 | Blaeser et al. | |
| 6,222,097 B1 | 4/2001 | McBride et al. | |
| 6,322,817 B1 | 11/2001 | Maitra et al. | |
| 6,331,186 B1 | 12/2001 | Wang et al. | |
| 6,364,856 B1 | 4/2002 | Ding et al. | |
| 6,478,814 B2 | 11/2002 | Wang et al. | |
| 6,497,729 B1 | 12/2002 | Moussy et al. | |
| 6,610,013 B1 | 8/2003 | Fenster et al. | |
| 6,696,089 B2 | 2/2004 | Kabanov et al. | |
| 6,773,447 B2 | 8/2004 | Laguna | |
| 6,838,528 B2 | 1/2005 | Zhao | |
| 6,897,205 B2 | 5/2005 | Beckert et al. | |
| 6,982,024 B2 * | 1/2006 | Shkolnik | A61M 25/1025 156/293 |
| 6,989,156 B2 | 1/2006 | Gillis | |
| 7,152,452 B2 | 12/2006 | Kokish | |
| 7,169,162 B2 | 1/2007 | Garakani | |
| 7,171,255 B2 | 1/2007 | Holupka et al. | |
| 7,308,748 B2 | 12/2007 | Kokish | |
| 7,335,184 B2 | 2/2008 | Laguna | |
| 7,378,144 B2 | 5/2008 | Demeo et al. | |
| 7,445,735 B2 | 11/2008 | Miller et al. | |
| 7,727,554 B2 | 6/2010 | Labhasetwar et al. | |
| 8,211,055 B2 | 7/2012 | Christiansen | |
| 8,257,722 B2 | 9/2012 | Michal et al. | |
| 8,343,498 B2 * | 1/2013 | Alexis | A61P 31/00 424/184.1 |
| 8,613,952 B2 | 12/2013 | Lee et al. | |
| 8,673,332 B2 | 3/2014 | Michal et al. | |
| 9,034,362 B2 | 5/2015 | Michal et al. | |
| 9,114,125 B2 | 8/2015 | Klein et al. | |
| 9,415,193 B2 | 8/2016 | Campbell et al. | |
| 10,314,948 B2 | 6/2019 | Michal et al. | |
| 2002/0064513 A1 | 5/2002 | Maitra et al. | |
| 2003/0054042 A1 | 3/2003 | Liversidge | |
| 2003/0059398 A1 | 3/2003 | Ranger et al. | |
| 2004/0006359 A1 | 1/2004 | Laguna | |
| 2004/0215315 A1 | 10/2004 | Jones et al. | |
| 2005/0177226 A1 | 8/2005 | Banik et al. | |
| 2005/0273075 A1 | 12/2005 | Krulevitch et al. | |
| 2006/0079836 A1 | 4/2006 | Holman et al. | |
| 2006/0280858 A1 | 12/2006 | Kokish | |
| 2007/0065481 A1 * | 3/2007 | Chudzik | A61L 29/085 424/426 |
| 2007/0255388 A1 | 11/2007 | Rudakov et al. | |
| 2008/0015500 A1 | 1/2008 | Herweck et al. | |
| 2008/0114331 A1 | 5/2008 | Holman et al. | |
| 2008/0140002 A1 * | 6/2008 | Ramzipoor | A61M 25/10 604/103.02 |
| 2008/0195042 A1 * | 8/2008 | Weber | A61F 2/04 604/103.02 |
| 2009/0227948 A1 | 9/2009 | Chen et al. | |
| 2009/0252724 A1 * | 10/2009 | Loetscher | C07K 16/18 424/133.1 |
| 2009/0254064 A1 | 10/2009 | Boatman | |
| 2009/0258049 A1 | 10/2009 | Klein et al. | |
| 2009/0269383 A1 | 10/2009 | Kuehling et al. | |
| 2010/0239635 A1 | 9/2010 | McClain et al. | |
| 2010/0312182 A1 | 12/2010 | Adden et al. | |
| 2010/0324645 A1 | 12/2010 | Stankus et al. | |
| 2011/0155664 A1 | 1/2011 | Kangas et al. | |
| 2011/0054396 A1 | 3/2011 | Kangas et al. | |
| 2011/0076315 A1 * | 3/2011 | Casanova | A61L 31/04 424/423 |
| 2011/0143014 A1 | 6/2011 | Stankus et al. | |
| 2011/0144582 A1 | 6/2011 | Stankus et al. | |
| 2011/0295200 A1 | 12/2011 | Speck et al. | |
| 2011/0301565 A1 | 12/2011 | Weber | |
| 2012/0059316 A1 | 3/2012 | Owens et al. | |
| 2012/0128863 A1 | 5/2012 | Nguyen et al. | |
| 2012/0143132 A1 | 6/2012 | Orlowski | |
| 2012/0150142 A1 | 6/2012 | Neber et al. | |
| 2012/0232640 A1 | 9/2012 | Hovers | |
| 2012/0277843 A1 * | 11/2012 | Weber | A61M 25/104 623/1.11 |
| 2012/0283636 A1 | 11/2012 | Rizq et al. | |
| 2012/0296274 A1 | 11/2012 | Slager | |
| 2013/0018448 A1 | 1/2013 | Folan et al. | |
| 2013/0187434 A1 | 8/2013 | Nang | |
| 2013/0197619 A1 * | 8/2013 | Ishii | B05B 13/0442 623/1.11 |
| 2013/0253426 A1 * | 9/2013 | Campbell | A61L 29/085 604/103.02 |
| 2013/0261545 A1 | 10/2013 | Osypka | |
| 2014/0012634 A1 | 1/2014 | Denison et al. | |
| 2014/0171912 A1 | 6/2014 | Gharib et al. | |
| 2015/0018866 A1 * | 1/2015 | Komatsu | A61M 25/1029 606/194 |
| 2015/0182732 A1 | 7/2015 | Zeng et al. | |
| 2015/0190430 A1 | 7/2015 | Lim | |
| 2015/0190618 A1 | 7/2015 | Kantor | |
| 2015/0250926 A1 * | 9/2015 | McClain | A61L 29/16 604/509 |
| 2015/0320910 A1 | 11/2015 | Klein et al. | |
| 2015/0320984 A1 * | 11/2015 | Davies, Jr. | D04C 1/06 604/103.09 |
| 2016/0022966 A1 | 1/2016 | Chuter | |
| 2016/0038322 A1 * | 2/2016 | Dorn | A61F 2/0095 623/1.12 |
| 2016/0166728 A1 | 6/2016 | Girdhar | |
| 2016/0250152 A1 | 9/2016 | Labhasetwar et al. | |
| 2017/0014553 A1 | 1/2017 | Antoni et al. | |
| 2017/0072116 A1 | 3/2017 | Antoni et al. | |
| 2017/0151420 A1 | 6/2017 | Laguna | |

(56) References Cited

U.S. PATENT DOCUMENTS

| | | |
|---|---|---|
| 2017/0360991 A1 | 12/2017 | Cleek et al. |
| 2019/0275210 A1 | 9/2019 | Michal et al. |

FOREIGN PATENT DOCUMENTS

| | | |
|---|---|---|
| CN | 104511084 | 4/2015 |
| EP | 0464163 B1 | 1/1992 |
| WO | 99/59649 A1 | 11/1999 |
| WO | 2001087227 | 11/2001 |
| WO | 2003/015677 A1 | 2/2003 |
| WO | 2008/064058 A2 | 5/2008 |
| WO | 2009070794 | 6/2009 |
| WO | 2009/131911 A2 | 10/2009 |
| WO | 2010/036694 A1 | 4/2010 |
| WO | 2010/036697 A1 | 4/2010 |
| WO | 2011061295 | 5/2011 |
| WO | 2012084024 | 6/2012 |
| WO | 2012122023 | 9/2012 |
| WO | 2013007273 | 1/2013 |
| WO | 2013074185 | 4/2013 |
| WO | 2013097717 | 4/2013 |
| WO | 2014127718 | 8/2014 |
| WO | 2014158516 | 10/2014 |
| WO | 2015077545 | 5/2015 |

OTHER PUBLICATIONS

Dave Fornell, "Companies Developing Drug-Eluting Balloons"; hllps://www.dicardiology.com/article/companies-developing-drug-eluting-balloons; May 3, 2010; 2 pages.

Granada, Biological Concepts and Lessons Learned from the PAC-COCATH Technology in Pre-Clinical Animal Models (2009); 26 pages.

Ron Waksman, et al. "Drug-Eluting Balloon, The Comeback Kid?" Contemporary Reviews in Interventional Cardiology; Gire Cardiovasc Intervent. 2009;2:352-358; 8 pages.

Reserach and Devlopmenl CARDIONOVUM, http://www.cardionovum.eu/research; 2013; 3 pages.

Thomas Zeller et al., "Drug-Eluting Balloon Versus Standard Balloon Angioplasty for Infrapoplileal Arterial Revascularization in Critical Limb Ischemia" Journal of the Amer Ican Colleg E of Cardiology, 2014, vol. 64, No. 15, 2014; 9 pages.

Seidlitz A, Kotzan IN, Nagel S, Reske T, Grabow N, Harder C, et al. (2013) In Vitro Determination of Drug Transfer from Drug-Coaled Balloons. PLoS ONE 8(12): e83992. doi:10.1371/journal.pone.0083992; 10 pages.

Kaule S, Minralh I, Stein F, Krag! U, Schmidt W, Schmitz K-P, et al. (2015) Correlating Coaling Characteristics with the Performance of Drug-Coaled Balloons—A Comparative In Vitro Investigation of Own Established Hydrogel- and onic Liquid-Based Coaling Matrices. PLoS ONE 10(3): e0116080. doi:10.1371/journal.pone.0116080; 11 pages.

Mohammadreza Mehdizadeh et al., "Design Strategies and Applications of Tissue Bioadhesives", Macromol Biosci. J013 March; 13(3): 271-288. doi:10.1002/mabi.201200332; 30 pages.

Amey S. Puranik, et al., "Recent Advances in Drug Eluting Stenls", Int J Pharrn. Jan. 30, 2013; 441 (1-2): 665-679. doi:10.1016/j.ijpharm.2012.10.029; 33 pages.

Serguei Vinogradov, et al. Nanogel Network for Delivery, "Nanogel carries drugs to targeted cells for better treatment" http://llechnologies.unemed.com/delivery/nanogel-network-delivery/; University of Nebraska; retrieved on Dec. 6, 2015;: pages.

Reddy et al., University of Nebraska Medical Center "Colloidal Drug Carrier System for Drug Eluting Balloons" 2008; 7 pages.

Nikol et al, Expanded Polytetralluoroethylene Membranes and Their Applications, Filtration and Purification in the Biopharmaceutical Industry, Second Ed. Chap. 23, pp. 619-640 Feb. 2008, 23 pages.

Lambert CR et al, "Local drug delivery catheters: functional comparison of porous and microporous designs."; Coron Artery Dis. May 1993;4{5):46975. Abstract; 2 pages.

Terry et al "In vivo evaluation of the delivery and efficacy of a sirolimusladen polymer gel for inhibition of hyperplasia in a porcine model of arteriovenous hemodialysis graft stenosis." J Control Release 160(3): 459-467 (2012); 23 pages.

Andreas Indermuehle et al. "Drug-eluting balloon angioplasty for in-stent restenosis: a systematic review and meta-analysis of randomised controlled trials"; Heart, published online Jan. 18, 2013; 9 pages.

N. Lemm, "Test for Porosity of Vascular Grails", S. Dawids {ed.),Test Procedures for the Blood Compatibility of Biomaterials, 75-77, 1993 Kluwer Academic Publishers; 3 pages.

Maxwell E. Afari, et al. "Mechanisms of Action in Drug-Coated Balloons" Aug. 2012 Endovascular Today, pp. 53-57.

Pedro A. Lemos, et al. "Emerging Technologies—Polymer free Phospholipid Encapsulated Sirolimus nano carriers for controlled Release"; EuroIntervention, vol. 9, No. 1, pp. 148-156, 10 pages.

Agent™ Paclitaxel Coated—PTCA Balloon Catheter, Boston Scientific, http://www.bostonscientific.com/en-EU/products/balloons-drug-coated/agent.html, 6 pages {retrieved on Nov. 21, 2018).

Boaz Mizrahi et al, "Elasticity and safety of alkoxyethyl cyanoacrylate tissue adhesives"; Acta Biomaterialia 7 (2011) 3150-3157; 9 pages.

Drug-Coated Balloon Superior to Conventional Angioplasty at Two Years in SFA, Diagnostic and Interventional Cardiology; Oct. 18, 2015; http://www.dicardiology.com/article/drug-coated-balloon-superior-conventional-angioplasty-two-years-sfa; 3 pages.

International Search Report and Written Opinion dated May 5, 2017 corresponding to International Patent Application No. PCT/US2017/016981; 16 pages.

Supplementary European Search Report dated Oct. 24, 2019 corresponding to European Patent Application No. EP 17 75 0680.

Noveon publication: "Polymers for Personal Care": TDS-114: May 1998.

Noveon publication: "Polymers for Personal Care": TDS-117: Apr. 1994.

Noveon publication: "Polymers for Personal Care": TDS-118: Apr. 1999.

Noveon publication: "Polymers for Personal Care": TDS-124: Apr. 1994.

Noveon publication: "Polymers for Personal Care": TDS-232-3: Mar. 1995.

Noveon publication: "Polymers for Personal Care": TDS-237: Oct. 1998.

Noveon publication: "Solutions Close to Home": PDS Pemulen 1622: Nov. 1999.

\* cited by examiner

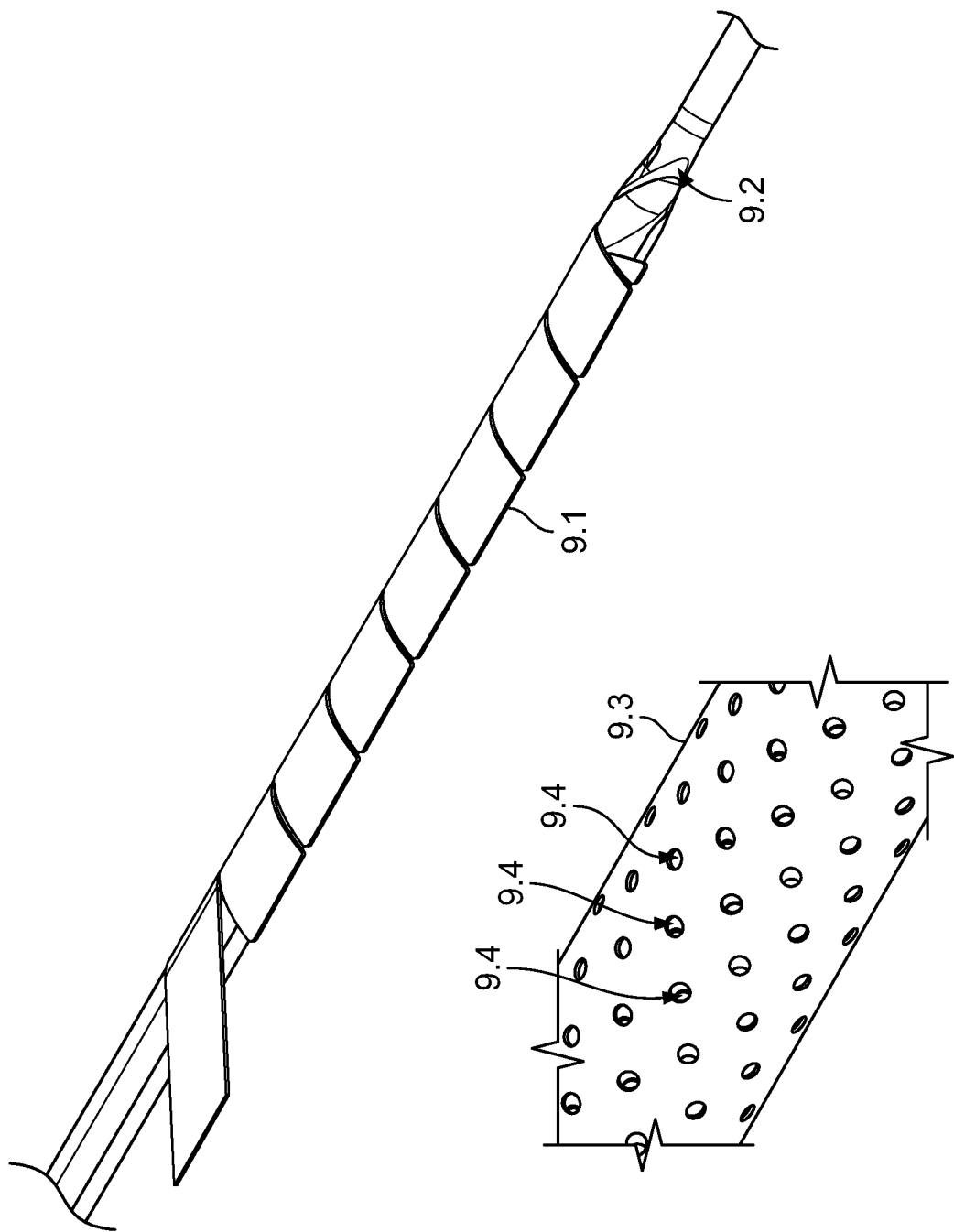

DRUG ELUTING BALLOON

FIELD OF THE INVENTION

The present invention is an inflatable balloon which is enclosed by an expandable cover which becomes increasingly porous/permeable during expansion. The balloon is coated or enclosed with a matrix which contains a pharmaceutically active agent. During expansion of the balloon, the pharmaceutically active agent is released or extruded through the expandable cover (e.g., a membrane) into a body cavity such as an artery or vein. The present invention also provides for a method of delivering the inflatable balloon as well as the pharmaceutically active agent to a body cavity.

BACKGROUND

Atherosclerosis involves a thickening of the arterial wall. Pathologically, atherosclerosis results from invasion and accumulation of white blood cells (also referred to as foam cells) and proliferation of intimal smooth muscle cell which forms a fibrofatty plaque in the arterial wall. Potentially, atherosclerosis can affect any arterial blood vessel, either centrally or peripherally, causing a narrowing or even complete obstruction of any artery. Angioplasty is a therapeutic technique involving mechanical widening of the obstructed artery.

Percutaneous coronary intervention (PCI), also known as coronary angioplasty, is a therapeutic procedure used to treat the narrowed or stenotic section of the coronary artery of the heart due to coronary lesions or obstructions. A guide catheter may be used in PCI to provide support and easier passage for another catheter or device (microcatheter, stents, balloons, etc.) to access the target site. For example, a guide catheter can be inserted through the aorta and into the ostium of the coronary artery. The guide catheter is then inserted into the opening or ostium of the artery to be treated and a guidewire or other instrument passed through the lumen of the guide catheter and inserted into the artery beyond the occlusion or stenosis. Peripherally, percutaneous transluminal intervention or PTA is used to treat narrowing or stenosis of arteries such as the iliac, femoral, popliteal, renal or carotid arteries. Neurovascular angioplasty is also growing in importance as a means for treating stroke.

In certain circumstances, a stent may be inserted into the blood vessel during angioplasty in order to maintain patency of the lumen. However, a known complication of stenting is restenosis, where the blood vessel narrows as a result of the invasion of smooth muscle cells and accumulation of the extracellular matrix in response to injury from angioplasty. In order to prevent restenosis, stents may be coated with a variety of different, antiproliferative pharmacological agents such as sirolimus (drug eluting stents). Although drug eluting stents have proved very effective at treating occluded coronary arteries, there remains a small, but measureable incidence of severe complications after stent implantation resulting from stent thrombosis. Luscher et al. *Circulation* 115:1051 (2007). Stent thrombosis has a very mortality and morbidity. Id.

Drug eluting balloons (DEB) offer an alternative to POBA (Plain Old Angioplasty Balloon), or bare or drug eluting stents. Importantly, DEB can provide several distinct advantages when compared with these other modes of intervention. Waksman et al. *Circulation: Cardiovascular Interventions* 2:352 (2009). For example, drug eluting stents do not work well with long tortuous vessels, small vessels (i.e., less then 2.5 mm in diameter) or in long, diffuse calcified lesions. Id. First generation DEB have been limited to the delivery of paclitaxel given the method and mechanics of drug transfer from the balloon surface to the vessel wall. Moreover, sustained release of paclitaxel is not required for a long lasting anti-proliferative effect. A drug eluting balloon allows for rapid delivery of a comparatively large quantity of drug over a short period of time. Other advantages of a drug eluting balloon include, (a) homogenous drug transfer to the entire vessel wall; (b) rapid release of high concentrations of the drug over periods no longer than a week; (c) absence of foreign body, i.e., stent, could decrease chronic inflammation and the trigger for late thrombosis; (d) absence of a stent allows the artery's original anatomy to remain intact, such as in cases of bifurcation or small vessels; and (e) with local drug delivery, dependence on antiplatelet therapy could be decreased. Id.

Thus, there is an on-going need to develop drug eluting balloons which can deliver drugs effectively to the vascular space or to any other body cavity over a sustained period of time.

SUMMARY OF THE INVENTION

The present invention is an inflatable balloon which is enclosed by an expandable cover which becomes increasingly porous or permeable during expansion. The balloon may comprise a coating. The coating may further comprise at least one pharmaceutical agent. The coating may be a biocompatible matrix. During expansion of the balloon, the pharmaceutically active agent is released through the expandable cover (e.g., a membrane) into a body cavity such as an artery or vein. The present invention also provides for a method of treating a condition or disease by delivering (or inserting) the inflatable balloon to a body cavity with subsequent delivery of a pharmaceutically active agent to the body cavity.

The inflatable balloon can be an angioplasty balloon which is positioned on a catheter or other flexible shaft device. The balloon is coated with at least one pharmaceutically active agent. The coating may be in the form of any biocompatible matrix. For example, the biocompatible matrix may be a semisolid such as a gel, a tape, a tube, spiral-cut tube or other form of wrapping. The pharmaceutically active agent may be suspended, embedded or dissolved in a biocompatible matrix. The pharmaceutically active agent may be miscible or immiscible with the biocompatible matrix. In certain embodiments, the pharmaceutically active agent may be encapsulated in one or more particles such as one or more, microspheres, liposomes, nanoparticles (e.g., nanogels) or other particles such as, cyclodextran. The gel may be a hydrogel which can be dried and then re-hydrated prior to the expansion of the balloon in vivo or in vitro.

In certain embodiments, the balloon and the biocompatible matrix are enclosed by an expandable cover which conforms to the balloon. The expandable cover may be semi-permeable or porous when the balloon is in an unexpanded state. In other embodiments, the expandable cover is substantially impermeable or non-porous when the balloon is in an unexpanded state.

When the balloon expands, permeability or porosity of the expandable cover to the external environment (e.g., plasma, blood, body fluid, etc.) increases. For example, during inflation of the balloon, the expansion of the balloon stretches or radially expands the expandable cover. As the balloon expands, pores or channels may form or may increase in size and/or number in the expandable cover. In certain embodiments, when the coated balloon is initially exposed to an aqueous environment, e.g., plasma or phosphate buffered saline, for a defined period of time, fluid is able to penetrate the expandable cover and begin to solubilize the biocompatible matrix. This initial solubilization of the biocompatible facilitates expansion of the coating (fluidizes) as the expandable balloon is inflated. As the balloon expands, plasma or other aqueous fluids, can continue to diffuse into the annular space or lumen between the expandable cover and the balloon. Upon inflation, the coating continues to dissolve, releasing the pharmaceutically active agent through the expandable cover into the body cavity, such as as the artery or vein. In one embodiment, the coating is initially dehydrated. Once in contact with the plasma or other aqueous fluid, the coating is rehydrated and then dissolved. The rate of release of the pharmaceutically active agent is variable and is dependent on a number of different factors, including the rehydration process and nature of the biocompatible matrix, the rate of extent of expansion of the balloon and the degree of porosity/permeability of the expandable cover.

The expandable cover may comprise a plurality of pores.

The permeability and/or porosity of the expandable cover in an expanded state is greater than the permeability and/or porosity of the expandable cover when it is in an unexpanded state. The permeability and/or porosity of the expandable cover in the expanded state may be at least 20% greater, at least 30% greater, at least 40% greater, at least 50% greater, at least 60% greater, at least 70% greater, at least 80% greater, at least 90% greater, at least 100% greater, at least 120% greater, at least 150% greater, at least 200% greater, at least 250% greater, at least 300% greater, or range from about 20% to about 400% greater, from about 50% to about 300% greater, or from about 100% to about 200% greater, as compared with the permeability and/or porosity of the expandable cover in an unexpanded state.

In one embodiment, the coating is or comprises a biocompatible matrix such as a hydrogel.

The pharmaceutical agent can be encapsulated in a plurality of microspheres, nanoparticles (e.g., nanogels), liposomes, or cyclodextran particles in the biocompatible matrix. In certain embodiments, the nanoparticle is formed from a nanogel which may be formed from N-isopropylacrylamide, N-vinyl pyrrolidone and pegylated maleic acid and combinations thereof.

In another embodiment, the coating is a thin film which can be formed from hydroxypropyl methylcellulose (HPMC), carboxymethyl cellulose (CMC), hydroxypropyl cellulose (HPC), poly (vinyl pyrrolidone) (PVP), poly (vinyl alcohol) (PVA), poly (ethylene oxide) (PEO), pullulan, chitosan, sodium alginate, carrageenan or gelatin. The coating may be in the form of a tape which can be wrapped around the balloon, e.g., in a spiral configuration.

In one embodiment, the expandable cover is formed from a polymer such as expanded poly(tetrafluoroethylene) (ePTFE) or ultra-high molecular weight polyethylene.

In certain embodiments, the total surface load of the pharmaceutically active agent in the coating on the balloon ranges from about 1 $\mu g/mm^2$ to about 50 $\mu g/mm^2$.

When the balloon is in an unexpanded state, less than about 10% (w/w) of the pharmaceutically active agent is released from the inflatable balloon in an unexpanded state, when the inflatable balloon is incubated for about one hour at 37° C. in an aqueous solution. In certain embodiments, when the balloon is expanded, greater than about 50% (w/w), greater than about 60% (w/w), greater than about 70% (w/w), greater than about 80% (w/w), greater than about 90% (w/w), or greater than about 95% (w/w), of the pharmaceutically active agent is released from the inflatable balloon in an expanded state, when the inflatable balloon is incubated for one hour in an aqueous solution at 37° C. In certain embodiments, about 100% (w/w) of the pharmaceutically active agent is released from the inflatable balloon in an expanded state when the inflatable balloon is incubated for one hour in an aqueous solution at 37° C.

When the balloon is expanded, the diameters of the pores range from about 1 $\mu m$ to about 100 $\mu m$ or about 20 $\mu m$ to about 80 $\mu m$.

The pharmaceutically active agent may be an anti-proliferative agent such as paclitaxel, everolimus, tacrolimus, sirolimus, zotarolimus, biolimus and rapamycin or mixtures thereof.

In one embodiment, the expandable cover is tubular in shape.

The inflatable balloon may be used to treat a disease or a condition. The method may involve inserting the inflatable balloon into a body cavity. The body cavity can be an artery such as a coronary, infrainguinal, aortoiliac, subclavian, mesenteric, basilar and renal artery. Alternatively, the body cavity can be a urethra, bladder, ureters, esophagus, stomach, colon, trachea, bronchi or alveoli.

In certain embodiments, the present disclosure provides for an inflatable balloon comprising at least one inflatable body portion and at least one pharmaceutically active agent. The inflatable body portion of the inflatable balloon is covered by a cover that is permeable to said pharmaceutically active agent at least when said inflatable body portion is in an expanded state, wherein said pharmaceutically active agent resides in between said body portion and said cover. During use of the inflatable balloon, said pharmaceutically active agent is released from said inflatable body portion.

In certain embodiments, said cover is an expandable cover, and wherein, when said cover is in an expanded state, a permeability of said cover is greater than the permeability of said cover when said cover is in a non-expanded state.

The device is an inflatable balloon which may be positioned on a catheter or other flexible shaft device. In an embodiment, the balloon segment of the catheter is encapsulated, coated or otherwise provided with at least one therapeutic or pharmaceutically active agent such as everolimus, tacrolimus, sirolimus, zotarolimus, biolimus, rapamycin or an equivalent active pramaceutical ingredient, which is encapsulated or suspended in a biocompatible matrix.

In certain embodiments, the pharmaceutically active agent can be embedded, layered, suspended or dissolved in a matrix such as gel. The gel or matrix may be a hydrogel which can be dried and re-hydrated prior to the expansion of the balloon in vivo. In one embodiment, the gel matrix comprises a hydratable suspension. In one embodiment, the gel matrix may be dehydrated.

In certain embodiments, the balloon and the matrix are encapsulated by an expandable cover.

The expandable cover may be a polymer membrane (or an expandable membrane), having a plurality pores (having an average size). In certain embodiments, the average size of said pores is greater in an expanded state of said membrane than in a non-expanded state of said membrane. In certain embodiments, the membrane is non-permeable or semi-permeable in an unexpanded state. When the balloon expands, the permeability of the cover may increase. For example, during inflation of the balloon catheter, the expansion of the balloon body stretches the membrane, and pores or channels may form in or throughout the cover which increase in diameter as the balloon expands. The diameter of the pores or material porosity may range from about 1 μm to about 100 μm, or from about 20 μm to about 80 μm or about 1 μm to 50 μm, when the membrane is expanded. The membrane may be hydrophobic and non-permeable when non-expanded while the matrix is being extruded through the membrane once the balloon is being inflated and exerts pressure on the matrix.

In certain embodiments, the inflatable balloon comprises a longitudinal axis and a plurality of pleats folded along the longitudinal axis of the balloon.

The balloon may be coated with at least one pharmaceutically active agent.

The cover may be formed as an expandable tubular sleeve that encloses the balloon, while being substantially compliant with said balloon in its non-inflated state. In certain embodiments, the cover comprises a tubular sleeve that is provided over at least said inflatable body portion of said balloon, and in that said cover lies substantially compliant with said body portion of the balloon in the non-inflated state of said balloon.

In certain embodiments, the cover may be formed from a braid.

The cover may comprise a porous layer (e.g., an elastomeric porous layer) having a porosity. In one embodiment, the porosity of said layer is greater in an expanded state of said layer than in a non-expanded state of said layer.

When expanded, the porosity of the expandable cover may be greater than the porosity of the expandable cover when it is in an unexpanded state. The expandable cover may have a plurality of pores. After expansion, the porosity of the expandable cover in the expanded state ranges from about 20% to about 400% greater, from about 50% to about 300% greater, or from about 100% to about 200% greater, as compared with the unexpanded state.

The pharmaceutically active agent is suspended in a matrix. The matrix can be a gel such as a hydrogel. During expansion of the balloon, the therapeutic agent is released to a body cavity such as a blood vessel or other bodily lumen.

The cover can be formed from a polymer such as ePTFE or ultra-high molecular weight polyethylene.

In certain embodiments, the pharmaceutically active agent may be suspended or encapsulated in a plurality of biodegradable nano-sized and/or micron-sized bodies, such as beads, spheres or cells that are several nanometers to a few micrometers in size. These biodegradable bodies may be suspended and distributed (e.g., homogeneously) in a (further) matrix. In one embodiment, the inflatable body portion of the balloon is coated with said matrix, containing said bodies. In one embodiment, the cover is coated with said matrix, containing said bodies. In one embodiment, said bodies are suspended in a soluble film, which may be wrapped around at least the inflatable body portion of said balloon. The said film may comprise a water degradable matrix that contains said bodies. In one embodiment, said film is a solvent cast or extruded thin film formulation containing said bodies. In one embodiment, said film comprises a polysaccharide polymer consisting of maltotriose units, inter alia known as pullulan. In one embodiment, said film contains between 5% and 30% (w/w) of the pharmaceutically active agent. In one embodiment, said film comprises one or more auxiliary agents from a group comprising stabilizers, thickening agents, and permeability enhancers.

Particularly said (further) matrix may be formed into a tube, spiral cut tubular construction, tape or film that may be wrapped around said inflatable portion of said balloon. The film may be a water-swellable dehydrated film that degrades and dissolves one (in vivo) in contact with water. The nano/micro bodies are then vented or pressed through the cover and into surrounding tissue of a body lumen, particularly an artery or vein, while the balloon is inflated in vivo and will then based on composition of drug release said pharmaceutically active agent over a prolonged period of time. Typically said prolonged period of time may be over 25 days, particularly over 30 days. The bodies may incorporate as much as between 5% w/w to 30% w/w of the active pharmaceutical ingredient.

The film may comprise a polysaccharide polymer consisting of maltotriose units, inter alia known as pullulan. Pullulan is a polysaccharide polymer consisting of maltotriose units, also known as α-1,4- ;α-1,6-glucan. Three glucose units in maltotriose are connected by an α-1,4 glycosidic bond, whereas consecutive maltotriose units are connected to each other by an α-1,6 glycosidic bond. Pullulan is produced from starch by the fungus Aureobasidium pullulans. Pullulan is mainly used by the cell to resist desiccation and predation. The presence of this polysaccharide also facilitates diffusion of molecules both into and out of the cell.

The film may comprise one or more auxiliary agents from a group comprising stabilizers, thickening agents and permeability enhancers.

In some embodiments, less than about 10% (w/w) of the pharmaceutically active agent is released from the balloon at body temperature in about one hour in an aqueous environment, when the balloon is non-inflated. In certain embodiments, greater than about 50% (w/w), 60% (w/w), 70% (w/w) or 80% (w/w) of the pharmaceutically active agent is released from the balloon at body temperature in about one hour in an aqueous environment (such as PBS), when the balloon is inflated.

In certain embodiments, the pharmaceutically active agent comprises an anti-proliferative agent such as everolimus, tacrolimus, sirolimus, zotarolimus, biolimus, rapamycin, an M-tor inhibitor active agent, or a pharmaceutically equivalent agent.

In certain embodiments, between 5% and 30% w/w of said pharmaceutically active agent is present in the matrix.

The present disclosure also provides for a catheter comprising the inflatable balloon as described herein.

BRIEF DESCRIPTION OF THE DRAWINGS

FIG. 9 shows the matrix formed as spiral wrap, enclosed with an expandable cover, and a close-up view of the balloon with extrusion of the gel through the pores/slits.

Figure 1:
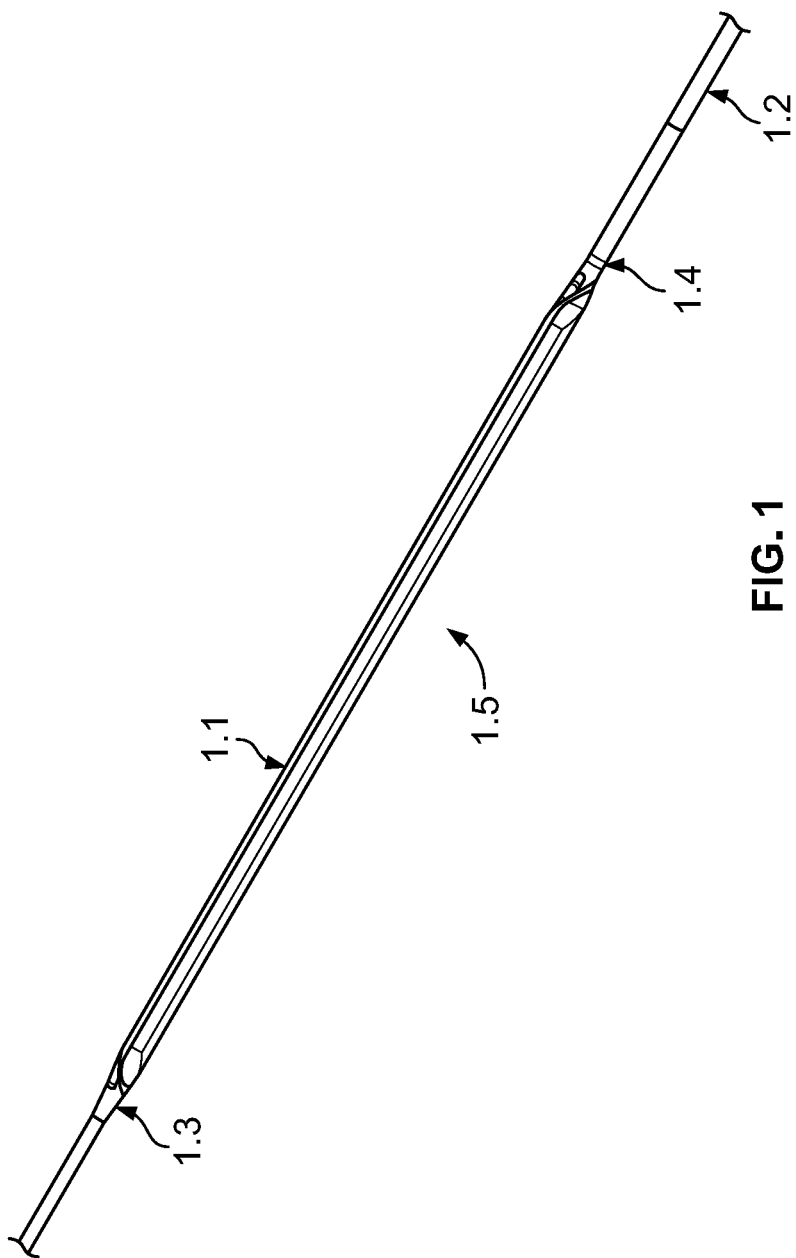
FIG. 1 shows the guidewire and the balloon in an unexpanded state.

(A) The balloon is shown with the tape wrapped around the proximal portion of the balloon.

(B) The balloon is shown with the tape wrapped around the distal portion of the balloon.

(C) The balloon is shown with four (4) wraps of the tape around the balloon.

(D) The balloon is shown with two different tapes, Tape 1 and Tape 2, wrapped around the balloon.

(E) The balloon is shown with two different tapes, Tape 1 and Tape 2, wrapped around the proximal, Tape 1, and distal, Tape 2, portions of the balloon.

(F) The Pullulan is shown with two different APIs, $APi_1$ and $API_2$, suspended in a nanoparticle, $API_1$ and a liposome, $API_2$.

(G) The balloon is shown with four different Tapes, Tapes 1-4, aligned longitudinally along the balloon.

DETAILED DESCRIPTION

The present disclosure provides for an inflatable balloon which is enclosed by an expandable cover which becomes increasingly porous/permeable during expansion. The balloon is coated or enclosed with a matrix that contains a pharmaceutically active agent. During expansion of the balloon, the pharmaceutically active agent is released through the expandable membrane into a body cavity such as an artery or vein. The present invention also provides for a method of treating a disease or condition by delivering the inflatable balloon to the artery, vein or body cavity.

The inflatable balloon can be an angioplasty balloon which is positioned on a catheter or other flexible shaft device. The balloon is coated with at least one pharmaceutically active agent. The coating may be in the form of any biocompatible matrix (as used herein, coating refers to coating, covering, enclosing or disposing (disposed) between the balloon and the expandable cover). For example, the biocompatible matrix may be a semisolid such as a gel. The coating incorporating the pharmaceutically active agent may also be wrapped around the balloon using a tape which may be in the form of a spiral, spiral-cut tube or spiral-cut wrapping enclosing the balloon. The balloon may be wrapped 1, 2, 3, 4, 5, 6, 7, 8, 9, 10 . . . n times with the biocompatible matrix. The pharmaceutically active agent may be suspended, embedded or dissolved in a biocompatible matrix such as gel. The pharmaceutically active agent may be miscible or immiscible with the biocompatible matrix. In certain embodiments, the pharmaceutically active agent may be encapsulated in a particle such as a liposome, nanoparticle or other particle such as, cyclodextran. The gel may be a hydrogel which can be dried and then re-hydrated prior to the expansion of the balloon in vivo or in vitro.

As used herein, the term "a pharmaceutically active agent" is interchangeable with the terms "a pharmaceutical agent" or "drug".

The balloon and the biocompatible matrix are enclosed by an expandable cover which conforms to the balloon (as used herein, enclosed, enclosing or encloses refers to surrounding, covering, enclosing or encapsulating). The expandable cover may entirely enclose the entire balloon or only a portion of the balloon. There exists an annular space or lumen between the expandable cover and the balloon which may be sealed, i.e., not in fluid communication with the catheter or alternatively, the annular space or lumen may be in fluid communication with the catheter. Preferably, the expandable cover is semi-permeable or porous when the balloon is in an unexpanded state. When the balloon expands, porosity or permeability of the expandable cover to the external environment, e.g., plasma, blood, body fluid, etc. increases. For example, during inflation of the balloon catheter, the expansion of the balloon stretches or radially expands the expandable cover. As a result of such expansion, pores or channels may form in the expandable cover; these pores or channels increase in size or number as the balloon expands. When the coated balloon is initially exposed to an aqueous environment, e.g., plasma or phosphate buffered saline, for a defined period of time, fluid is able to penetrate the expandable cover and begin to solubilize the matrix. This initial solubilization facilitates expansion of the coating (fluidizes) as the expandable balloon is inflated. As the balloon expands, plasma or other aqueous fluids, can continue to diffuse into the annular space or lumen between the expandable cover and the balloon. Upon inflation, the coating continues to dissolve, releasing the pharmaceutically active agent through the expandable cover into the body cavity, such as as the artery or vein (as used herein, release refers to release, extrusion, squeezing, burst or diffusion of the pharmaceutically active agent either alone or encapsulated in a microsphere, liposome, nanoparticle (e.g., nanogel), cyclodextran or other particle or in conjunction with the biocompatible matrix through the expandable cover). In one embodiment, the coating is initially dehydrated. Once in contact with the plasma or other aqueous fluid, the coating becomes fully rehydrated and then dissolves. The rate of release of the pharmaceutically active agent is variable and is dependent on a number of different variables, including the rehydration process and nature of the biocompatible matrix, the rate of extent of expansion of the balloon and the degree of porosity/permeability of the expandable cover.

Diseases that can be treated with the present balloon, include, but are not limited to, both coronary artery and peripheral artery diseases as well as others. Non-limiting examples of the diseases or conditions that can be treated by the present balloon or method include atherosclerosis, coronary artery atherosclerosis disease (CAD), peripheral artery atherosclerosis disease (PAD), narrowing of an artery, etc.

Atherosclerosis is one of the leading causes of death and disability in the world. Atherosclerosis involves the deposition of fatty plaques on the luminal surface of arteries. The deposition of fatty plaques on the luminal surface of the artery causes narrowing of the cross-sectional area of the artery. Ultimately, this deposition blocks blood flow distal to the lesion causing ischemic damage to the tissues supplied by the artery. Coronary arteries supply the heart with blood. Coronary artery atherosclerosis disease (CAD) is the among most common, serious, chronic, life-threatening illness in the United States. According to the Centers for Disease Control, 370,000 people die annually from CAD and 735,000 Americans have a heart attack or myocardial infarction (https://www.cdc.gov/heartdisease/facts.htm, retrieved, Feb. 5, 2017). Narrowing of the coronary artery lumen causes destruction of heart muscle resulting first in angina, followed by myocardial infarction and finally death.

Narrowing of the arteries can occur in vessels other than the coronary arteries, including carotid, aortoiliac, infrainguinal, distal profunda femoris, distal popliteal, tibial, subclavian and mesenteric arteries. The prevalence of peripheral artery atherosclerosis disease (PAD) depends on the particular anatomic site affected as well as the criteria used for diagnosis of the occlusion, but as many 8.5 million people in the United States are estimated to suffer from PAD (https://www.cdc.gov/dhdsp/data_statistics/fact_sheets/fs-_pad.htm, retrieved, Feb. 5, 2017). Traditionally, physicians have used the test of intermittent claudication to determine whether PAD is present.

The present invention also provides for a method of treating any body cavity by releasing a pharmaceutically active agent from an inflatable balloon through an expandable cover into body cavities other than vascular spaces. For example, the genitourinary system, including, the urethra, bladder, ureters, penis and vagina, gastrointestinal system, such as the esophagus, stomach, small intestine or colon, the respiratory system, including, the trachea, bronchi and alveoli can be treated with the balloon of the present invention. Vascular spaces other than coronary arteries may also be treated, including, the aorta, vena cava (inferior and superior) or neurovascular arteries, e.g., carotid arteries, basilar arteries. The coated balloon of the present invention may also be used to create a cavity within a potential space in the body, e.g., muscle, vascular intima or fibrotic tissue. The pharmaceutically active agent is then released into the new body cavity created from the potential space, e.g., within a muscle.

Other diseases may be treated with the coated balloon of the present invention, including, inflammatory diseases and cancers. Cancers that can be treated with coated balloon of the present invention include, but are not limited to, bladder, lung cancer, ear, nose and throat cancer, leukemia, colon cancer, melanoma, pancreatic cancer, mammary cancer, prostate cancer, breast cancer, hematopoietic cancer, ovarian cancer, basal cell carcinoma, biliary tract cancer; bladder cancer; bone cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lymphoma including Hodgkin's and Non-Hodgkin's lymphoma; myeloma; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

Inflammatory diseases, include, but are not limited to, rheumatoid arthritis, systemic lupus eythematosis (SLE), Crohn's diseases or other collagen vascular diseases. Infections diseases resulting from bacteria, viruses or prions may also be treated with the balloon of the present invention.

The structure of the expandable cover is preferably elastically compliant and expandable. The expandable cover may be constructed in the form of a weave, sheet, tube, film, cast, sleeve, tape or any other desired structural configuration which permits the expandable cover to be conformal to the balloon. The expandable cover further comprises a plurality of holes, pores, slits or perforations. Alternatively, the holes, pores, slits or perforations may be formed from a porous network of fibrils, or from a variable density of a fibril matte. Various types of expandable covers may be used, including those which are elastomeric and where the pores open when the balloon is inflated (and/or the cover is expanded), and retract when the balloon is deflated (and/or the cover is unexpanded). The expandable cover may comprise, e.g. silicone, latex, polyurethane, and those other materials which are plastically deformed as the material is stretched, thus opening up pores (see discussion of materials, infra.). When the expandable cover is in an unexpanded state, the holes, pores, slits or perforations are substantially closed, so that the permeability of the expandable cover as measured by release of the pharmaceutically active agent from the balloon (e.g., into an aqueous environment) is less than about 50% (w/w), less than about 25% (w/w), less than about 15% (w/w), less than about 10% (w/w), or less than about 5% (w/w) over a defined period of time as set for the below. As used herein, w/w means the weight of the pharmaceutically active agent released at any time, t, over total weight of pharmaceutically active agent coated on the balloon; % w/w means w/w×100.

In vivo release of the pharmaceutically active agent into a vascular space may be simulated in vitro by incubating the balloon which is coated with a pharmaceutically active agent and enclosed with an expandable cover in an aqueous bath including a buffer such as phosphate buffered salined (PBS). The release of the pharmaceutically active agent to the aqueous bath (e.g., the buffer) after expansion of the balloon is then assayed. Release profiles, both absolute w/w as well as kinetic $$J = -D\frac{dC}{dx}$$

(see discussion below), of the pharmaceutical active agent are measured. The concentration of the pharmaceutically active agent in the aqueous environment may be measured using any means, including, but not limited to, high pressure liquid chromatography (HPLC) or specific immunological assays. For example, the amount of the pharmaceutically active agent released through the expandable cover within about 1 hour when incubated at about 4° C., about 20-25° C. or about 37° C. in an aqueous environment such as PBS, plasma, blood, a body fluid, or other aqueous medium is assayed. Various time points may be used to assess release of the pharmaceutically active agent when the balloon is in an unexpanded state or an expanded state, including, but not limited to, within about 30 seconds, within about 1 minute, within about 2 minutes, within about 3 minutes, within about 4 minutes, within about 5 minutes, within about 6 minutes, within about 8 minutes, within about 9 minutes, within about 10 minutes, within about 15 minutes, within about 20 minutes, within about 25 minutes, within about 30 minutes, within about 35 minutes, within about 40 minutes, within about 45 minutes, within about 50 minutes, within about 55 minutes, within about 1 hour, within about 2 hours, within about 3 hours, within about 4 hours, within about 5 hours, within about 6 hours, within about 7 hours, within about 8 hours, within about 1-10 minutes, within about 10-100 minutes or within about 50 -200 minutes.

After the expandable balloon has been advanced to the target site, the operator, e.g., the interventional cardiologist, deploys the balloon by inflating it. When the expandable cover is expanded due to expansion of the balloon, the porosity or permeability of the expandable cover increases. As discussed previously, plasma or other aqueous fluids can then diffuse into the annular space or lumen between the expandable cover and the balloon. The coating is then dissolved (totally or partially), releasing the pharmaceutically active agent through the expandable cover into the body cavity, such as as the artery or vein to the pharmaceutically active agent. In one embodiment, the coating is initially dehydrated during application to the balloon and then rehydrated after contact with the aqueous environment, e.g., plasma. When the expandable cover is in an expanded state, the permeability of the expandable cover as measured by release of the pharmaceutically active agent into an aqueous environment is about 100% (w/w), 95% (w/w), 90% (w/w), 80% (w/w), 70% (w/w), 60% (w/w), 50%

(w/w), 40% (w/w), 30% (w/w) or 20% (w/w). The assay for the pharmaceutically active agent can be performed as described above at 4° C., 20-25° C. or 37° C. in an aqueous environment such as PBS at 1 hour or for the time periods set forth above.

Any desired amount of pharmaceutically active agent can be applied to the balloon. For example, the amount of the pharmaceutically active agent that is coated on or impregnated on the balloon (e.g., the cover and/or matrix) may range from about 10 to 50,000 µg, including, 10, 20, 30, 40, 50, 60, 70, 80, 90, 100, 500, 1000, 10,000, 20,000, 30,000, 40,000 and 50,000 µg. The total surface load of the pharmaceutically active agent on the balloon may range from about 1 µg/mm² to about 200 µg/mm², including, about 1, 2, 3, 4, 5, 6, 7, 8, 9, 10, 20, 30, 40, 50, 100, 150 or 200 µg/mm². The amounts of the active agent present on the balloon in the biocompatible matrix can range from 2 µg/mm² to 10 µg/mm², 2.5 µg/mm² to 5 µg/mm², 1 µg/mm² to 2 µg/mm², 2 µg/mm² to 15 µg/mm², 5 µg/mm² to 25 µg/mm² or 25 µg/mm² to 40 µg/mm². Because the coating can be applied in any form, e.g., a tape or wrapping and the annular space or lumen between the balloon and expandable cover may vary as well. Accordingly, the quantity of the pharmaceutically active agent may vary significantly, with loadings of the pharmaceutically active agent ranging up to 10,000 -50,000 µg.

Permeability of the expandable cover may be a function of the porosity of the expandable cover. When the expandable cover is in an expanded state, the permeability or porosity of the expandable cover may range from about 20% to about 400%, from about 50% to about 300%, or from about 100% to about 200% greater than the permeability or porosity of the expandable cover when the expandable cover is in an unexpanded or compressed state. To calculate % ranges here, the permeability or porosity in the expanded state is divided by the permeability or porosity, respectively, in the unexpanded state and then multiplied by 100. Percentage differences also include, 10%, 20%, 30%, 40%, 50% 60% 70%, 80%, 90% 100%, 150%, 200%, 250%, 300%, 400%, 500%, 600%, 700%, 800% and the like.

"Porosity" refers to a measure of the void spaces in a material, and is measured as a percentage of void space to solid material ranging between 0-100%. Porosity may be determined according to the equation: Porosity=$(1-d_1/d_2) \times 100$, where $d_1$ is the density of the material which is determined from the material weight and the material volume as ascertained from measurements of the sample dimensions, and $d_2$ is the density of the solid portion of the sample (see, e.g., U.S. Pat. No. 7,445,735 and EP 0464163B1). The volume of the solid portion of the sample can be measured, for example, using a Quantachrome stereopycnometer (Quantachrome Corp.). The average diameter of the pores of the expandable structure can be determined by mercury intrusion porosimetry using an Autoscan mercury porosimeter (Quantachrome Corp.). Mercury Intrusion/Extrusion is based on forcing mercury (a non-wetting liquid) into a porous material under tightly controlled pressures. Since mercury does not wet most substances and will not spontaneously penetrate pores by capillary action, it must be forced into the voids of the sample by applying external pressure. The pressure required to fill the voids is inversely proportional to the size of the pores. Only a small amount of force or pressure is required to fill large voids, whereas much greater pressure is required to fill voids of very small pores. U.S. Pat. No. 7,445,735. The porosimetry can also be conducted using other suitable non-wetting liquid besides mercury. Other methods that may be employed to measure porosity include ellipsometric porosimetry, water saturation method, water evaporation method, and nitrogen gas adsorption method. The diameters of the pores in the expandable cover when expanded may range from about 1 µm to about 100 µm, from about 10 µm to about 100 µm, from about 20 µm to about 80 µm, from about 40 µm to about 60 µm or about 20 µm to about 50 µm.

The pharmaceutically active agent can be uniformly delivered over a period of time, t, to the body cavity. The pharmaceutically active agent may be released through the expandable cover following zero-order kinetics with no burst effect. As used herein, the term "zero-order kinetics" refers to a release profile where the pharmaceutically active agent is released at a rate independent of time and the concentration of the pharmaceutically active agent incorporated into the balloon. Zero-order release ensures that a steady amount of pharmaceutically active agent is released over desired length of time, minimizing potential peak/ trough fluctuations and side effects, while maximizing the amount of time the pharmaceutically active agent's concentrations remain within the therapeutic window. The release rate may be calculated using standard methodology, $$J = -D \frac{dC}{dx}$$

Where drug flux is J and the change in drug concentration over time can be represented as:

$$\frac{\partial C}{\partial t} = D \frac{\partial^2 C}{\partial x^2}$$

The term "drug", "pharmaceutically active agent" or "pharmaceutical agent" are used interchangeably here. Release rates may also be diffusion or erosion driven. Fu et al. *Drug Release Kinetics and Transport Mechanisms of Non-degradable and Degradable Polymeric Delivery Systems.* Expert Opin Drug Deliv. 2010 April; 7(4): 429-444. Alternatively, the release of the pharmaceutically active agent may act as a burst with immediate release into the body cavity.

The thickness of the expandable cover may range from about 0.1 µm to about 300 µm or from about 1 µm to about 150 µm. Other ranges are included herein, such as 50, 100, 150, 200, 250 or 300 µm. The expandable cover deforms without cracking when it is subjected to stretch or elongation and undergoes plastic and/or elastic deformation. After the balloon is deflated, the expandable cover returns to its unexpanded state without being broken, torn, inverted or rolled-back onto itself. The expandable cover may comprise any suitable materials, including synthetic and non-synthetic materials. The expandable cover may also comprise mixtures of synthetic and non-synthetic materials. Examples of the synthetic material, include high density, high molecular weight polyethylene (HDHMWPE), ultra high molecular weight polyethylene (UHDHMWPE), expanded poly(tetrafluoroethylene) (ePTFE), ethylene vinyl acetate, latexes, urethanes, fluoropolymer, polyvinyl alcohol (PVA)-cross linked hydrogel, polysiloxanes, styrene-ethylene/butylene-styrene block copolymers, aliphatic polyesters, and mixtures and copolymers thereof, polydimethylsiloxane (PDMS) (Silicone) or polyurethane foam, e.g., HYPOL™. The expandable material may be woven as a braid with a latticework of polymeric monofilaments such as a tubular interbraided sleeve of polymeric multifilament yarns. U.S. Pat. No. 5,957,974.

In one embodiment, the expandable cover is constructed of medical grade silicone. In another embodiment, the cover is an elastomer. In a third embodiment, the elastomer is a high-strength thermoplastic elastomer. This high-strength thermoplastic elastomer can be a styrenic block copolymer, a polyolefin blend, an elastomeric alloy, a thermoplastic polyurethane, a thermoplastic copolyester, or a thermoplastic polyamide. The high-strength thermoplastic elastomer may be formed from a polyester-polyether copolymer or a polyamide-polyether copolymer. The high-strength thermoplastic elastomer can also be a nylon. Examples of the non-synthetic material include, but are not limited to, collagen, fibrin, elastin, extracellular matrix components as well as mixtures thereof.

The coating may be in the form of any biocompatible matrix. The coating may be applied directly on the exterior surface of the balloon, or may be applied on the interior or inner surface of the expandable cover. Alternatively, the pharmaceutically active agent may be disposed between the outer surface of the balloon and interior or inner surface of the expandable cover in a biocompatible matrix. The coating incorporating the pharmaceutically active agent may also be wrapped around the balloon using a tape which may be in the form of a spiral, spiral-cut tube or spiral-cut wrapping enclosing the balloon. The balloon may be wrapped 1, 2, 3, 4, 5, 6, 7, 8, 9, 10 . . . n times with the biocompatible matrix. The biocompatible matrix containing the pharmaceutically active agent can be applied to the balloon or expandable cover using standard techniques to cover either the entire or only a partial surface of the balloon or the expandable cover. The coating may form a single layer of a homogeneous mixture of a pharmaceutically active agent(s) and a biocompatible matrix, e.g., gel, or be present in a defined geometric pattern, e.g., a dot matrix pattern.

The coating may form a single layer or multiple layers such as a continuous wrapping around the balloon. The balloon may be dipped or sprayed with a liquid solution comprising at least one pharmaceutically active agent. After each layer is applied, the balloon may be dried before application of the next layer. The thickness of the layer incorporating the pharmaceutically active agent may range from about 0.1 µm to about 150 µm, from about 1 µm to about 100 µm, from about 10 µm to about 50 µm, or from about 20 µm to about 30 µm. Alternatively, multiple layers of the pharmaceutically active agent/biocompatible matrix composition can be applied on the surface of the balloon or cover in these or other thickness ranges. For example, different layers of two or more pharmaceutically agents can be coated on the balloon or expandable cover so that a particular pharmaceutically active agent can be released into the body cavity first, followed by subsequent release of a second pharmaceutically active agent.

The biocompatible matrix may comprise a water soluble material or water-swellable material. The pharmaceutically active agent may be dispersed uniformly or nonuniformly (e.g., particulates such as liposomes or nanoparticles) within the biocompatible matrix. The biocompatible matrix may comprise a water soluble material which may be dehydrated after application and then rehydrated after insertion into the body cavity by the operator. "Water soluble material" refers to material that dissolves, hydrolyzes, breaks-down, dissolves or disintegrates in contact with water or other aqueous physiological fluid, such as plasma or interstitial fluid. As the balloon expands, the expandable cover also expands, accompanied by an increase in permeability to the plasma or other physiological fluids. The water soluble material within the pharmaceutically active agent coating dissolves and the pharmaceutically active agent is released into the body cavity. The length of time that is needed for the biocompatible matrix to be dissolved may vary and be less than about 4 hours, 2 hours, less than about 1 hour, less than about 30 minutes, less than about 10 minutes, less than about 5 minutes, less than about 1 minute, less than about 30 seconds or less than about 5 seconds.

The biocompatible matrix may comprise a mixture of water insoluble and water soluble materials. Examples of such combinations, include shellac and polyvinylpyrollidone, and ethyl cellulose and hydroxypropylmethyl cellulose. The biocompatible matrix may also comprise water swellable material. Water soluble or water swellable material may comprise a polysaccharide, such as dextran, alginate, amylose, amylopectin, carrageenan, carboxymethyl cellulose, gellan, guar gum, polysaccharide conjugate vaccines, hydroxyethyl cellulose, hydroxypropyl cellulose, hydroxypropylmethyl cellulose, carboxymethyl cellulose, amylopectin, starch derivatives, hyaluronic acid, starch derivatives, xantan, xyloglucan, chitosan-based hydrogel, peptidoglycan, and progeogl yeans. Water soluble or water swellable material may also comprise a simple carbohydrate, such as glucose, maltose, lactose, fructose, sucrose, galactose, glucosamine, galactosamine, muramic acid, glucruronate, gluconate, fucose, trehalose, a synthetic polymer, such as polyvinyl alcohol, polyvinylpyrrolidone, polyethylene glycol, propylene glycol, polyoxyethylene derivatives, a polypeptide, such as elastin, polyvinyl amine or poly(L-lysine), uncrosslinked hydrogel, crosslinked hydrogel, polyacrylic acid or any other cross-linked water swellable polymers. Examples of hydrogel materials include carboxymethyl cellulose (CMC), hydroxypropylmethyl cellulose (HPMC), amylopectin, starch derivatives, hyaluronic acid, or their combinations (WO2007US0074123).

The biocompatible matrix that incorporates the pharmaceutical agent may also comprise any desired biocompatible, non-toxic material. Examples of such biocompatible materials include, poly(lactide-co-glycolide), polyesters such as polylactic acid, polyglycolic acid, polyanhydride, polycaprolactone, polyhydroxybutyrate valerate, or mixtures or copolymers thereof. In one embodiment, the biocompatible matrix may further comprise naturally occurring substances such as collagen, fibronectin, vitronectin, elastin, laminin, heparin, fibrin, cellulose, carbon or extracellular matrix components. Polymers which can be used in the matrix include poly(lactide-co-glycolide); poly-DL-lactide, poly-L-lactide, and/or mixtures thereof and can be of various inherent viscosities and molecular weights. In one embodiment, poly(DL lactide-co-glycolide) can be used. The poly-DL-lactide material can be in the form of homogeneous composition and when solubilized and dried, it can form a lattice of channels in which pharmaceutical substances can be trapped for delivery to the tissues. In a further embodiment, the coating composition comprises a nonabsorbable polymer, such as ethylene vinyl acetate (EVAC), polybutylmethacrylate (PBMA) and methylmethacrylate (MMA).

Other examples of bioabsorbable polymers that may be used with the methods of the present invention include, aliphatic polyesters, bioglass cellulose, chitin collagen copolymers of glycolide, copolymers of lactide, elastin, tropoelastin, fibrin, glycolide/l-lactide copolymers (PGA/PLLA), glycolide/trimethylene carbonate copolymers (PGA/TMC), hydrogel lactide/tetramethylglycolide copolymers, lactide/trimethylene carbonate copolymers, lactide/-ε- caprolactone copolymers, lactide-σ-valerolactone copolymers, L-lactide/d1-lactide copolymers, methyl methacrylate-N-vinyl pyrrolidone copolymers, modified proteins, nylon-2 PHBA/γ-hydroxyvalerate copolymers (PHBA/HVA), PLA/polyethylene oxide copolymers, PLA-polyethylene oxide (PELA), poly (amino acids), poly (trimethylene carbonates), poly hydroxyalkanoate polymers (PHA), poly(alklyene oxalates), polybutylene diglycolate), poly(hydroxy butyrate) (PHB), poly(n-vinyl pyrrolidone), poly(ortho esters), polyalkyl-2-cyanoacrylates, polyanhydrides, polycyanoacrylates, polydepsipeptides, polydihydropyrans, poly-d1-lactide (PDLLA), polyesteramides, polyesters of oxalic acid, polyglycolide (PGA), polyiminocarbonates, polylactides (PLA), polyorthoesters, poly-p-dioxanone (PDO), polypeptides, polyphosphazenes, polysaccharides, polyurethanes (PU), polyvinyl alcohol (PVA), poly-β-hydroxypropionate (PHPA), poly-β-hydroxybutyrate (PBA), poly-σ-valerolactone, poly-β-alkanoic acids, poly-β-malic acid (PMLA), poly-ε-caprolactone (PCL), pseudo-Poly(Amino Acids), starch, trimethylene carbonate (TMC) and tyrosine based polymers. U.S. Pat. No. 7,378,144.

Polymers used for controlled drug delivery may also be used with the coating. Examples of such polymers, include, polyanhydrides and polyesters, polymers and copolymers of lactic acid, glycolic acid, hydroxybutyric acid, mandelic acid, caprolactone, sebacic acid, 1,3-bis(p-carboxyphenoxy) propane (CPP), bis-(p-carboxyphenoxy)methane, dodecandioic acid (DD), isophthalic acid (ISO), terephthalic acid, adipic acid, fumaric acid, azeleic acid, pimelic acid, suberic acid (octanedioic acid), itaconic acid, biphenyl-4,4'-dicarboxylic acid and benzophenone-4,4'-dicarboxylic acid. Polymers may be aromatic, aliphatic, hydrophilic or hydrophobic.

The polymer forming the biocompatible matrix may comprise a polysaccharide polymer consisting of maltotriose units, also referred to as pullulan. Pullulan is a polysaccharide polymer consisting of maltotriose units, also known as α-1,4- ;α-1,6-glucan. Three glucose units in maltotriose are connected by an α-1,4 glycosidic bond, whereas consecutive maltotriose units are connected to each other by an α-1,6 glycosidic bond. Pullulan may be produced from starch by the fungus *Aureobasidium pullulans*.

The pharmaceutically active agent may be dispersed within and/or on a sponge-like membrane or layer, made of a non-hydrogel polymer having a plurality of voids. The sponge like membrane or layer alternatively may also be constructed out of a polymer based fibril network or scaffolding, resulting in void spaces existing within this fibrous or fibril nodal network. The pharmaceutically active agent may be infused into the voids of the sponge membrane or layer that is positioned on the external surface of the balloon and lie or be disposed between the outer membrane of the balloon and the inner wall of the expandable cover. When the balloon is radially expanded, the sponge membrane or layer stretches around the circumference of the balloon and becomes thinner, opening and enlarging the voids. As a result, the pharmaceutically active agent is expelled or "squeezed out" through the voids of the sponge membrane or layer. The sponge membrane or layer may be prepared by dissolving a non-hydrogel polymer in a solvent and an elutable particulate material. After the sponge membrane or layer composition is cured, it is exposed to a solvent, e.g. water or PBS, which causes the particulate material to elute from the polymer, leaving a sponge membrane or layer having a plurality of voids therein. The sponge coating is then exposed to a biologically active material to load the sponge membrane or layer with such material. Such material may be loaded into the coating by diffusion or other means. Non-hydrogel polymer(s) useful for forming the sponge membrane or layer are biocompatible. Non-hydrogel polymers are polymers that when a drop of water is added on top of a film of such polymer, the drop will not spread. Examples of such polymers include, without limitation, polyurethanes, polyisobutylene and its copolymers, silicones, and polyesters. Other suitable polymers include polyolefins, polyisobutylene, ethylene-alphaolefin copolymers, High Density High Molecular Weight Polyethelene (HDHMWPE), acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers. U.S. Pat. No. 6,773,447. U.S. Patent Publication No. 20040006359.

The biocompatible matrix may also comprise an organogel, such as a poly(ethylene), L-alanine, sorbitan monostearate, Eudragit or lecithin organogel. Gupta et al. *World J. Pharmacy & Pharmaceutical Sciences* 3(9):150-163 (2014). Alternatively, the gels may comprise a sol-gel. Niederberger et al. *Metal Oxide Nanoparticles in Organic Solvents, Synthesis, Formulation. Assembly and Applications.* Springer (2009).

The biocompatible matrix may comprise a thin film. Karki et al. Thin films as an emerging platform for drug delivery. Asian J. Pharmaceutical Sciences 574 (2016). Thin films comprise a thin and flexible layer of polymer with or without a plasticizer. Id. In certain embodiments, a thin film dissolves more rapidly, i.e., quick-dissolve, than other conventional dosage forms. Id. Thin films may also be mucoadhesive. Id. The thin film may be formed in any shape or size. In certain embodiments, the thin films may have a thickness of about 500 μm to about 1,500 μm; and when dried the thin films may have a thickness from about 3 μm to about 250 μm. The thin film may comprise polymers including, but not limited to, Hydroxypropyl methylcellulose (HPMC), Carboxymethyl cellulose (CMC), Hydroxypropyl cellulose (HPC), Poly (vinyl pyrrolidone) (PVP), Poly (vinyl alcohol) (PVA), Poly (ethylene oxide) (PEO), Pullulan, Chitosan, Sodium alginate, Carrageenan, Gelatin, or combinations thereof.

The biocompatible matrix may comprise a bioadhesive. The bioadhesive may be distributed throughout the biocompatible matrix or only around the particles containing the pharmaceutical agent (see discussion of pharmaceutically active agent which may be incorporated into a microsphere, liposomes, nanogels and other types of particle-based drug delivery vehicles which are incorporated in the matrix, infra). In certain embodiments, the bioadhesive adheres to the vessel or body cavity wall. For example, the bioadhesive may comprise an alginate-catechol mixture. Kastrup et al. PNAS 109: 21444-21449 (2012). In certain embodiments, the bioadhesive may comprise one or more hydrocolloid emulsifying agents. Non-limiting examples of hydrocolloid emulsifying agents that may be used include cellulosic emulsifying agents and acrylic emulsifying agents, including, for example, those which have an alkyl group containing from about 10 to about 50 carbon atoms. In certain embodiments, the acrylic emulsifying agents are copolymers of a carboxylic acid and an acrylic ester (described, for example, in U.S. Pat. Nos. 3,915,921 and 4,509,949), including those which are cross-linked. An example of such cross-linked emulsifying agent is "acrylates/$C_{10-30}$ alkyl acrylate crosspolymer", a cross-linked polymer of acrylic acid and ($C_{10-30}$) alkyl acrylates. Acrylates/$C_{10-30}$ alkyl acrylate crosspolymer is available from Noveon, Inc. (previously B. F. Goodrich) and is sold under the trade name Pemulen®. Acrylates/$C_{10-30}$ alkyl acrylate crosspolymer has a small lipophilic portion and a large hydrophilic portion, thus allowing for it to function as a primary emulsifier for the formation of oil-in-water emulsions. In addition, acrylates/$C_{10-30}$ alkyl acrylate crosspolymer is capable of releasing the compounds of the dispersed phase upon contact with a substrate, namely, biological membranes or mucosa and will not re-wet (the oil phase will not re-emulsify upon contact with water). Additional information regarding acrylates/$C_{10-30}$ alkyl acrylate crosspolymer, which is listed in the U.S. Pharmacopeia, is provided in Noveon publications TDS-114, 117, 118, 124, 232-3, and 237, and PDS Pemulen 1622.

Alkyl chain cyanoacrylates such as methyl-, ethyl-, isopropyl, butyl and octylcyanoacrylate may be used as bioadhesives. U.S. Pat. No. 8,613,952; see also, Mizrahi et al. *Acta Biomaterialia* 7:3150-3157 (2011). Other possible bioadhesives include, but are not limited to, urethane-based materials as well as adhesives incorporating mussel adhesive proteins. Mehdizadeh et al. *Macromol Biosci.* 13(3):271-288 (2013).

In certain embodiments, the bioadhesive can be prepared by combining: (i) a biopolymer having one or more first chemically reactive amine groups; (ii) a biocompatible crosslinker having at least two second chemically reactive groups that can chemically react with the one or more first chemically reactive amine groups of the biopolymer; and (iii) a biocompatible rheological modifier. U.S. Patent Publication No. 20160166728.

The biocompatible matrix may be mixed with a pharmaceutical acceptable excipient, e.g., a carrier, adjuvant and/or diluent, according to conventional pharmaceutical compounding techniques. The excipients for modifying, maintaining or preserving, include, for example, the pH, osmolarity, viscosity, clarity, color, isotonicity, odor, sterility, stability, rate of dissolution or release, adsorption or penetration of the composition. Suitable excipients include, but are not limited to, amino acids (such as glycine, glutamine, asparagine, arginine or lysine); antimicrobials; antioxidants (such as ascorbic acid, sodium sulfite or sodium hydrogen sulfite); buffers (such as borate, bicarbonate, Tris HCl, citrates, phosphates, other organic acids); bulking agents (such as mannitol or glycine), chelating agents (such as ethylenediamine tetraacetic acid (EDTA), ethylene glycol tetraacetic acid (EGTA)); complexing agents (such as caffeine, polyvinylpyrrolidone, beta cyclodextrin or hydroxypropyl beta cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (in one aspect, sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

The pharmaceutically active agent may be incorporated into a microsphere, liposomes, nanogels and other types of particle-based drug delivery vehicles which are incorporated in the biocompatible matrix. Hoare et al. *Polymer* 49:1993-2007 (2008). For example, Poly(lactic-co -glycolic acid) nanoparticles can be incorporated within a cross-linkable hyaluronan-based hydrogel matrix. Id.

Liposomes are microscopic lipid vesicles that are composed of a central aqueous cavity surrounded by a lipid membrane formed by concentric bilayer(s) (lamellas). Liposomes are able to incorporate hydrophilic substances (in the aqueous interior) or hydrophobic substances (in the lipid membrane). Liposomes can be unilamellar vesicles ("UMV"), having a single lipid bilayer, or multilamellar vesicles ("MLV"), having a series of lipid bilayers (also referred to as "oligolamellar vesicles"). The multilamellar vesicles typically range in size from 0.2 µm to 10 µm in diameter. See e.g., WO 98/006882. The bilayer(s) of liposomes most often comprise phospholipids, but may also comprise lipids including, but not limited to fatty acids, fatty acid salts and/or fatty alcohols. The properties of the liposomes depend, among other factors, on the nature of the constituents. Consequently, if liposomes with certain characteristics are to be obtained, the charge of its polar group and/or the length and the degree of saturation of its fatty acid chains must be taken into account. In addition, the properties of liposomes may be modified, e.g., to incorporate cholesterol and other lipids into the membrane, change the number of lipidic bilayers, or covalently join natural molecules (e.g., proteins, polysaccharides, glycolipids, antibodies, enzymes) or synthetic molecules (e.g., polyethyl glycol) to the surface. There are numerous combinations of phospholipids, optionally with other lipids or cholesterol, in an aqueous medium that can be used to obtain liposomes. Depending on the method of preparation and the lipids used, it is possible to obtain vesicles of different sizes, structures, and properties.

For example, the liposome can be formed from a homologous population of a phospholipid, such as a neutral phospholipid, or a mixture of different types of phospholipids. Examples of phospholipid for making the delivery vehicle include, but are not limited to, phosphatidylcholine (PC), phosphatidylglycerol (PG), phosphatidylethanolamine (PE), phosphatidylserine (PS), phosphatidic acid (PA), phosphatidylinositol (PI), egg phosphatidylcholine (EPC), egg phosphatidylglycerol (EPG), egg phosphatidylethanolamine (EPE), egg phosphatidylserine (EPS), egg phosphatidic acid (EPA), egg phosphatidylinositol (EPI), soy phosphatidylcholine (SPC), soy phosphatidylglycerol (SPG), soy phosphatidylethanolamine (SPE), soy phosphatidylserine (SPS), soy phosphatidic acid (SPA), soy phosphatidylinositol (SPI), dipalmitoylphosphatidylcholine (DPPC), 1,2-dioleoyl-snglycero-3-phosphatidylcholine (DOPC), dimyristoylphosphatidylcholine (DMPC), dipalmitoylphosphatidylglycerol (DPPG), diolelphosphatidylglycerol (DOPG), dimyristoylphosphatidylglycerol (DMPG), hexadecylphosphocholine (HEPC), hydrogenated soy phosphatidylcholine (HSPC), distearoylphosphatidylcholine (DSPC), distearoylphosphatidylglycerol (DSPG), dioleylphosphatidylethanolamine (DOPE), palmitoylstearoylphosphatidylcholine (PSPC), palmitoylstearoylphosphatidylglycerol (PSPG), monooleoylphosphatidylethanolamine (MOPE), 1-palmitoyl-2-oleoyl-sn-glycero-3-phosphatidylcholine (POPC), polyethyleneglycol distearoylphosphatidylethanolamine (PEG-DSPE), dipalmitoylphosphatidylserine (DPPS), 1,2-dioleoyl-sn-glycero-3-phosphatidylserine (DOPS), dimyristoylphosphatidylserine (DMPS), distearoylphosphatidylserine (DSPS), dipalmitoylphosphatidic acid (DPPA), 1,2-dioleoyl-sn-glycero-3-phosphatidic acid (DOPA), dimyristoylphosphatidic acid (DMPA), distearoylphosphatidic acid (DSPA), dipalmitoylphosphatidylinositol (DPPI), 1,2-dioleoyl-sn-glycero-3-phosphatidylinositol (DOPI), dimyristoylphosphatidylinositol (DMPI), distearoylphosphatidylinositol (DSPI), and a mixture thereof.

Alternatively, the pharmaceutically active agent may be incorporated into a nanogel. Vinogradov et al. *Expert Opin. Drug Deliv.* 4(1):5-17(2007). Nanogels are a polymer network of charged polyionic segments cross-linked by polyethylene glycol (PEG) segments. U.S. Pat. No. 6,696,089. A wide variety of different pharmaceutically active agents can be incorporated into the nanogel. Id.

The pharmaceutically active agent may be in the form of a nanoparticulate suspension, a solid lipid nanoparticle, PLGA nanoparticles or LyoCells® can be incorporated into or encapsulated in the biocompatible matrix. Hoare et al. *Hydrogels in drug delivery: Progress and Challenges.* Polymer 49:1993-2007 (2008).

The nanogel may be a nanoparticle composed of a cross-linked hydrophilic polymer network (hydrogel). Nanogels are most often composed of synthetic polymers or biopolymers which are chemically or physically cross-linked which are biocompatible. In yet another embodiment, the nanogels are biodegradable. Methods of obtaining nanogels are known in the art as well as methods for obtaining nanogels that are biocompatible and/or biodegradable (see U.S. Pat. No. 7,727,554). In one aspect, the nanogel comprises a linker that is biodegradable (e.g., wherein enzymes (e.g., physiological enzymes) can degrade the crosslinker, thereby degrading the nanogel). U.S. Patent Publication No. 20160250152. Nanogels (e.g., biodegradable nano gels) can be synthesized using polymers (e.g., N-isopropylacrylamide, N-vinyl pyrrolidone, pegylated maleic acid or a combination thereof) with a disulfide cross-linker. Nanogels formed using, for example, the above polymers may be about 50 nm in diameter with sustained drug release properties. Nanogels may be formed from N-alkylacrylamide. In a particular aspect, the N-alkylacrylamide is poly-N-isopropylacrylamide. The nanogel can further comprises a vinyl monomer and a polyalkylene glycol. For example, the vinyl monomer can be vinyl pyrrolidone and the polyalkylene glycol can be polyethylene glycol. The nanogel can further comprise sodium acrylate. In particular aspects, the nanogel comprises about 500 to about 1000 mg N-alkylacrylamide. In other aspect, the nanogel can comprise about 100 to about 200 mg of the vinyl polymer and about 50 to about 100 mg of the polyalkylene glycol. In yet other aspect, the nanogel comprises about 200 mg sodium acrylate. The size of the nanogel particles may vary, ranging from a particle diameter of about 10 nm, 20 nm, 40 nm, 60 nm, 80 nm, 100 nm, 120 nm, 140 nm, 160 nm, 180 nm, 200 nm, 220 nm, 240 nm, 260 nm, 280 nm, 300 nm, 320 nm, 340 nm, 360 nm, 380 nm, 400 nm, 420 nm, 440 nm, 460 nm, 480 nm, 500 nm, 520 nm, 540 nm, 560 nm, 580 nm, 600 nm, 620 nm, 640 nm, 660 nm, 680 nm, 700 nm, 720 nm, 740 nm, 760 nm, 780 nm, 800 nm, 820 nm, 840 nm, 860 nm, 880 nm, 900 nm, 920 nm, 940 nm, 960 nm, 980 nm or about 1000 nm. In other aspect, the nanogel has a zeta potential from about −10 mV, −15 mV, −20 mV, −25 mV, −30 mV, −35 mV, or −40 mV. The nanogel has a loading potential of about 2%, 3%, 4%, 5%, 6%, 7%, 8%, 9%, 10%, 15%, 20% or 25% of the pharmaceutically active agent.

In certain embodiments, the pharmaceutically active agent can be encapsulated in a cyclodextrin particles containing cellulose ether with a particle size in the range of 50 to 1000 μm. Cyclodextrins are oligomers of anhydroglucose units, which are linked via alpha-1,4 linkages into a ring shaped molecule. Depending upon the number of the units one refers to these as alpha (6 unit), beta (7 unit) and gamma (8 unit) cyclodextrin. These are conventionally produced from starch by enzymatic processes. The torroidal structure of the cyclodextrin makes possible the formation of an enclosing complex on a molecular level.

Pharmaceutically active agents that may be used in the present invention include: (i) pharmacological agents such as, (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as sirolimus (or its analogs, biolimus, everolimus or zotarolimus), paclitaxel, 5-fluorouracil, cisplatin, vinblastine, vincristine, epothilones, endostatin, angiostatin, angiopeptin, monoclonal antibodies capable of blocking smooth muscle cell proliferation, thymidine kinase inhibitors, rapamycin, 40-0-(2-Hydroxyethyl)rapamycin (everolimus), 40-0-Benzyl -rapamycin, 40-0(4'-Hydroxymethyl)benzyl-rapamycin, 40-0-[4'-(1,2-Dihydroxyethyl)]benzyl-rapamycin, 40-Allyl-rapamycin, 40-0-[3'-(2,2-Dimethyl-1,3-dioxolan-4(S)-yl-prop-2'-en-1'-yl]-20 rapamycin, (2':E,4'S)-40-0-(4',5'.:Dihydroxypent-2'-en-1'-yl), rapamycin 40-0(2Hydroxy) ethoxycar-bonylmethyl-rapamycin, 40-0-(3-Hydroxypropyl-rapamycin 40-0-((Hydroxy)hexyl-rapamycin 40-0-[2(2-Hydroxy)ethoxy]ethyl-rapamycin, 40-0-[(3S)-2,2Dimethyl-dioxolan-3-yl]methyl-rapamycin, 40-0-[(2S)-2,3-Dihydroxyprop-1-yl]-rapamycin, 40-0-(2-Acctoxy)ethyl-rapamycin, 40-0-(2-Nicotinoyloxy)ethyl-rapamycin, 40-0-[2-(N-25 Morpholino) acetoxyethyl-rapamycin, 40-0-(2-N-Imidazolylacetoxy)ethyl-rapamycin, 40-0[2-(N-Methyl-N'-piperazinyl)acetoxylethyl-rapamycin, 39-0-Desmethyl-3.9, 40-0,0 ethylene-rapamycin, (26R)-26-Dihydro-40-0-(2-hydroxy)ethyl-rapamycin, 28-O Methyrapamycin, 40-0-(2-Aminoethyl)-rapamycin, 40-0-(2-Acetaminoethyl)-rapamycin 40-0(2-Nicotinamidoethyl)-rapamycin, 40-0-(2-(N-Methyl-imidazo-2' ylcarbcthoxamido)ethyl)-30 rapamycin, 40-0-(2-Ethoxycarbonylaminoethyl)-rapamycin, 40-0-(2-Tolylsulfonamidoethyl)-rapamycin, 40-0-[2-(4',5'-Dicarboethoxy-1',2';3'-triazol-1'-yl)-ethyl]rapamycin, 42-Epi-(telrazolyl)rapamycin (tacrolimus), and 4243-hydroxy-2-(hydroxymethyl)-2-methylpropanoate]rapamycin (temsirolimus) (WO2008/086369) (in various embodiments, the macrolide immunosuppressive drug may be at least 50%, 75%, 90%, 98% or 99% crystalline; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and, (o) agents that interfere with endogenous vasoactive mechanisms, (ii) genetic therapeutic agents include anti-sense DNA and RNA as well as DNA coding for (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor a and P, platelet-derived endothelial growth factor, platelet-derived growth factor, tumor necrosis factor a, hepatocyte growth factor and insulin-like growth factor, (d) cell cycle inhibitors including CD inhibitors, and (e) thymidine kinase ("TK") and other agents useful for interfering with cell proliferation.

Other pharmaceutically active agents that can be used, include, acarbosc, antigens, beta-receptor blockers, non-steroidal antiinflammatory drugs (NSAID;, cardiac glycosides, acetylsalicylic acid, virustatics, aclarubicin, acyclovir, cisplatin, actinomycin, alpha- and beta-sympatomimetics, (dmeprazole, allopurinol, alprostadil, prostaglandins, amantadine, ambroxol, amlodipine, methotrexate, S-aminosalicylic acid, amitriptyline, amoxicillin, anastrozole, atenolol, azathioprine, balsalazide, beclomcthasone, betahistine, bezafibrate, bicalutamide, diazepam and diazepam derivatives, budesonide, bufexamac, buprcnorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidinc, cotrimoxazole, codeine, caffeine, vitamin D and derivatives of vitamin D, colestyramine, cromoglicic acid, coumarin and coumarin derivatives, cysteine, cytarabine, cyclophosphamide, cyclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafmil, orlistat, peptide antibiotics, phenytoin, riluzoles, risedronate, sildenafil, topiramatc, macrolide antibiotics, oestrogen and oestrogen derivatives, progestogen and progestogen derivatives, testosterone and testosterone derivatives, androgen and androgen derivatives, ethenzamide, etofenamate, ctofibrate, fcnofibrate, etofylHne, etoposide, famciclovir, famotidine, felodipine, fenoftbrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mcpindolol, meprobamate, meropenem, mesalazinc, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastinc, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralin, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tctracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazolinc, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobutcrol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, Zolpidem, zoplicone, zotipine and the like. See, e.g., U.S. Pat. Nos. 6,897,205, 6,838,528 and 6,497,729.

In certain embodiments, mesenchymal stem cell particles, such as exosomes, may be incorporated into the biocompatible matrix or otherwise coated on the balloon. U.S. Patent Publication No. 2015190430. Mesenchymal stem cell particles may be produced or from a mesenchymal stem cell (MSC). Such a method may comprise isolating the particle from a mesenchymal stem cell conditioned medium (MSC-CM). For example, the mesenchymal stem cell particle may be isolated based on molecular weight, size, shape, composition or biological activity. The conditioned medium may be filtered or concentrated or both during, prior to or subsequent to separation and use. MSCs-derived exosomes may be used to treat cardiovascular disease, including, myocardial infarction, reperfusion injury and pulmonary hypertension. Huang et al. Exosomes in Mesenchymal Stem Cells, a New Therapeutic Strategy for Cardiovascular Diseases? *Int J Biol Sci.* 11(2):238-245 (2015).

Alternatively, a variety of DNA or RNA vectors may be incorporated into the biocompatible matrix. For example, recombinant viruses include recombinant adeno-associated virus (AAV), recombinant adenoviruses, recombinant lentiviruses, recombinant retroviruses, recombinant poxviruses, and other known viruses in the art, as well as plasmids, cosmids, and phages may be used. Options for gene delivery viral constructs are well known in the art (see, e.g., Ausubel et al., Current Protocols in Molecular Biology, John Wiley & Sons, New York, 1989; Kay, M. A., et al., 2001 *Nat. Medic.* 7(1):33-40; and Walther W. and Stein U., 2000 Drugs, 60(2): 249-71). Additionally, delivery vehicles such as nanoparticle-and lipid-based mRNA or protein delivery systems can be used as an alternative to AAV vectors. Further examples of alternative delivery vehicles include lentiviral vectors, lipid-based delivery system, gene gun, hydrodynamic, electroporation or nucleofection microinjection, and biolistics. Various gene delivery methods are discussed in detail by Nayerossadat et al. (*Adv Biomed Res.* 2012; 1: 27) and Ibraheem et al. (*Int J Pharm.* 2014 Jan. 1; 459(1-2):70-83).

The present invention may be used with any balloon catheter stent delivery system, including balloon catheter stent delivery systems described in U.S. Pat. Nos. 6,168,617, 6,222,097; 6,331,186; 6,478,814; 7,169,162 or 20090254064.

The expandable cover may enclose the entire balloon or only a portion of the balloon. There exists an annular space or lumen between the expandable cover and the balloon which may be sealed, i.e., not in fluid communication with the catheter or alternatively, may be in fluid communication with the catheter shaft. For example, the balloon catheter system can allow for the release of a fluid into the space or annular lumen between the balloon and the expandable cover. In this embodiment, the annular lumen or space is in communication with a fluid delivery lumen extending along the catheter shaft and the anular lumen or space between the inflatable balloon and the expandable cover. Fluid passed through the fluid delivery lumen in the catheter shaft may be released into the annular lumen or space hydrating the dehydrated biocompatible matrix prior to or during insertion into the body cavity.

Balloon catheters such as those described in U.S. Patent Pub. No. 20040006359 may also be used with the methods of the present invention.

The coating can be applied to a balloon either after the balloon has been compacted for insertion or before insertion. The balloon is compacted by, e.g., crimping or folding. U.S. Pat. Nos. 5,350,361, 7,308,748 or 7,152,452. The balloon is delivered to the intervention site by a delivery device such as a catheter. Balloons can be delivered, removed, and visualized during delivery and/or removal by methods well known in the art, see, e.g., U.S. Pat. Nos. 6,610,013 or 7,171,255. The balloons of the present invention can include, compliant (expand, e.g., 16-40%, when pressurized), semi-compliant (expand, e.g., 7-16%, when pressurized), and non-compliant balloons (expand, e.g., 2-7%, when pressurized). The various characteristics, e.g., maximum distensions, i.e. distension from nominal diameter to burst, vary and are well known in the art. Cutting balloons which are also used in angioplasty may be used with the methods and devices of the present invention. The balloon is inflated to a set inflation pressure which is determined by the operator depending on the site and type of balloon. The "rated burst pressure" or "RBP" of the balloon is the maximum guaranteed pressure to which a balloon can be inflated without failing.

The balloon may be coated with a lubricant coating before or after application of the pharmaceutically active agent to reduce the coefficient of friction between the pharmaceutically active agent or biocompatible matrix and the balloon, i.e., sticking. The lubricant coating may be a hydrophilic or hydrophobic coat. Examples of lubricants to reduce the coefficient of friction used in medical devices include: silicone; colloidal solution of water and lecithin; polyphenyl ethers as electrical connector lubricants; and the solid lubricants molybdenum disulphide, PTFE or powdered graphite and boron nitride. The friction coefficients may be reduced as low as 0.001 or less. Alternatively, polymers having non-sticky surfaces can be produced by using a surface modifying compound such as Teflon®, fluoro-containing polymers and copolymers, and the like with vinyl terminal or side groups for chemical solvent resistance and non-sticky surfaces. Polymers having hydrophilic surfaces can be produced by using a surface modifying compound such as polyvinylpyrrolidone, PVA, PEG, and the like. In addition, polymers having a low surface friction can be produced by using a surface modifying compound such as polyvinylpyrrolidone, PVA, PEG, Teflon®, and the like.

Figure 2:
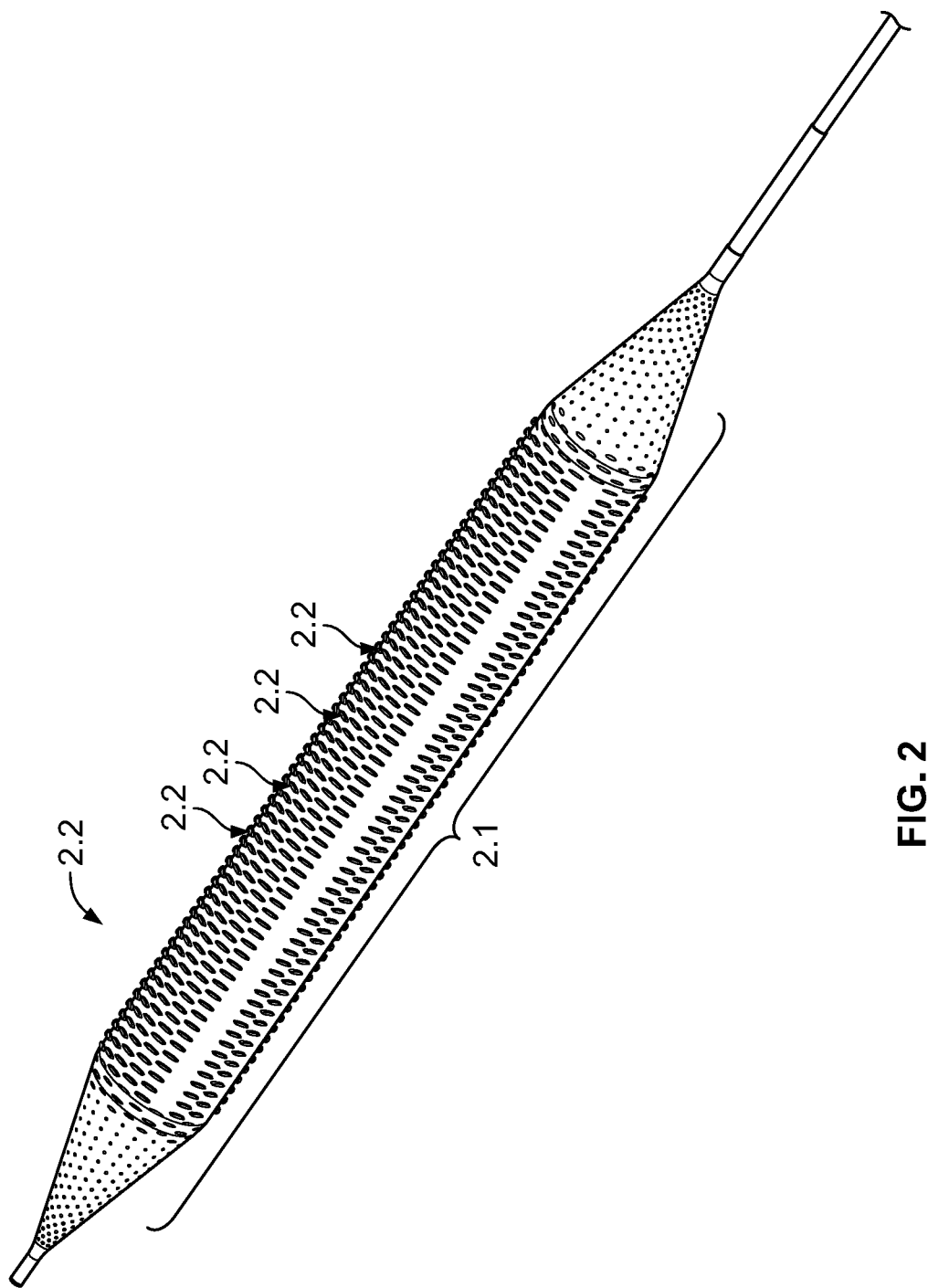
FIG. 2 shows the balloon in an expanded state.
Figure 3:
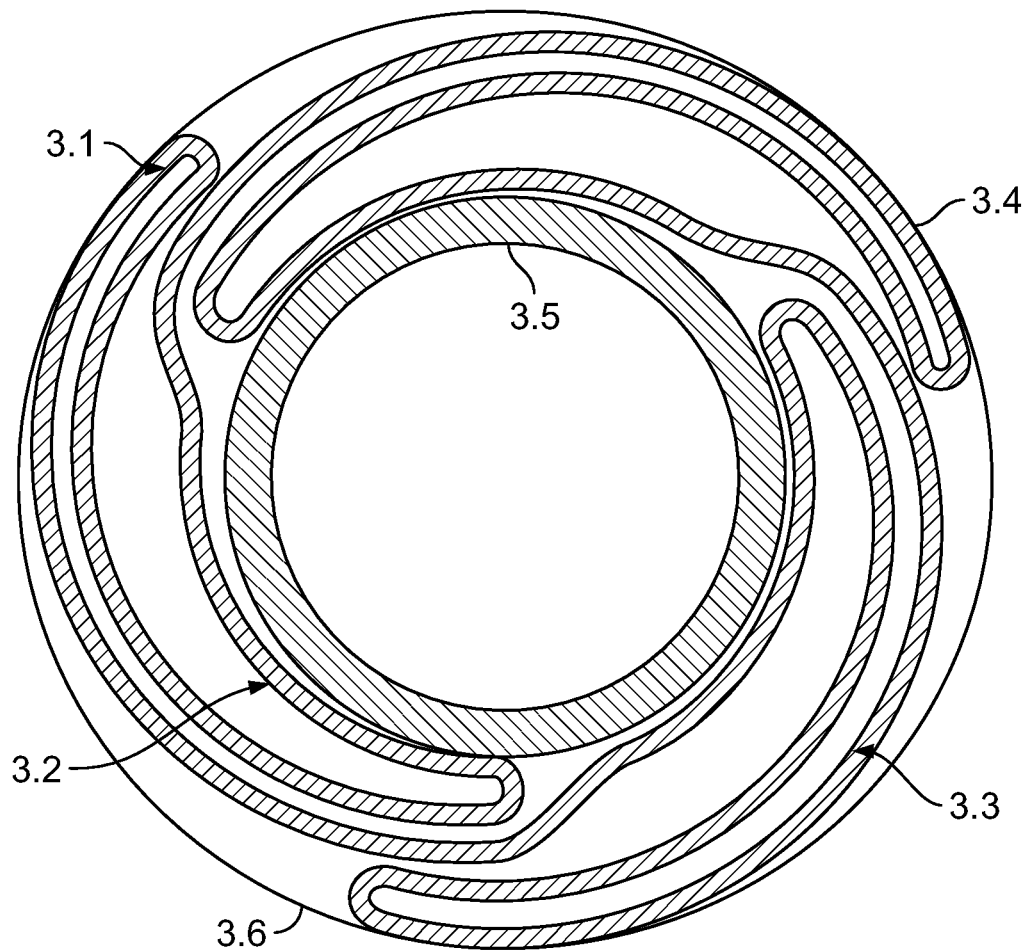
FIG. 3 shows a cross sectional view of the balloon in an unexpanded state with pleats and an expandable cover.

In one embodiment, the balloon 1.1 is positioned on a guidewire 1.2 (FIG. 1). The guidewire 1.2 can have marker bands 1.3, 1.4 positioned at either end of the balloon. The balloon can be in an expanded or inflated 2.1 (FIG. 2), allowing release or extrusion of biocompatible matrix or hydrogel 2.2. After introduction into the blood vessel, the balloon may be positioned adjacent to an atherosclerotic plaque. The balloon is introduced into the blood vessel or body cavity in a folded or pleated (or uninflated) state prior to inflation, 3.1, 3.2, 3.3, 3.4 with each 3.3, 3.2, 3.3 and 3.4 referring to the pleats as shown in FIG. 3 (guidewire 3.5) (FIG. 3). The balloon is completely enclosed or enveloped in an expandable cover 3.6. As the balloon inflates, the pleats unfold and after full expansion, the balloon is completely unfolded (inflated). In the unexpanded state, the pleats of the balloon wrap around the body of the balloon which is positioned over the guidewire. The balloon may contain 3, 4, 5, 6, 7, 8, 9, 10 . . . n pleats; the pleated size ratio to the inflated balloon can be 2, 3, 4, 5, 6, 7, 8, 9, 10, 20 or 30.

Figure 4:
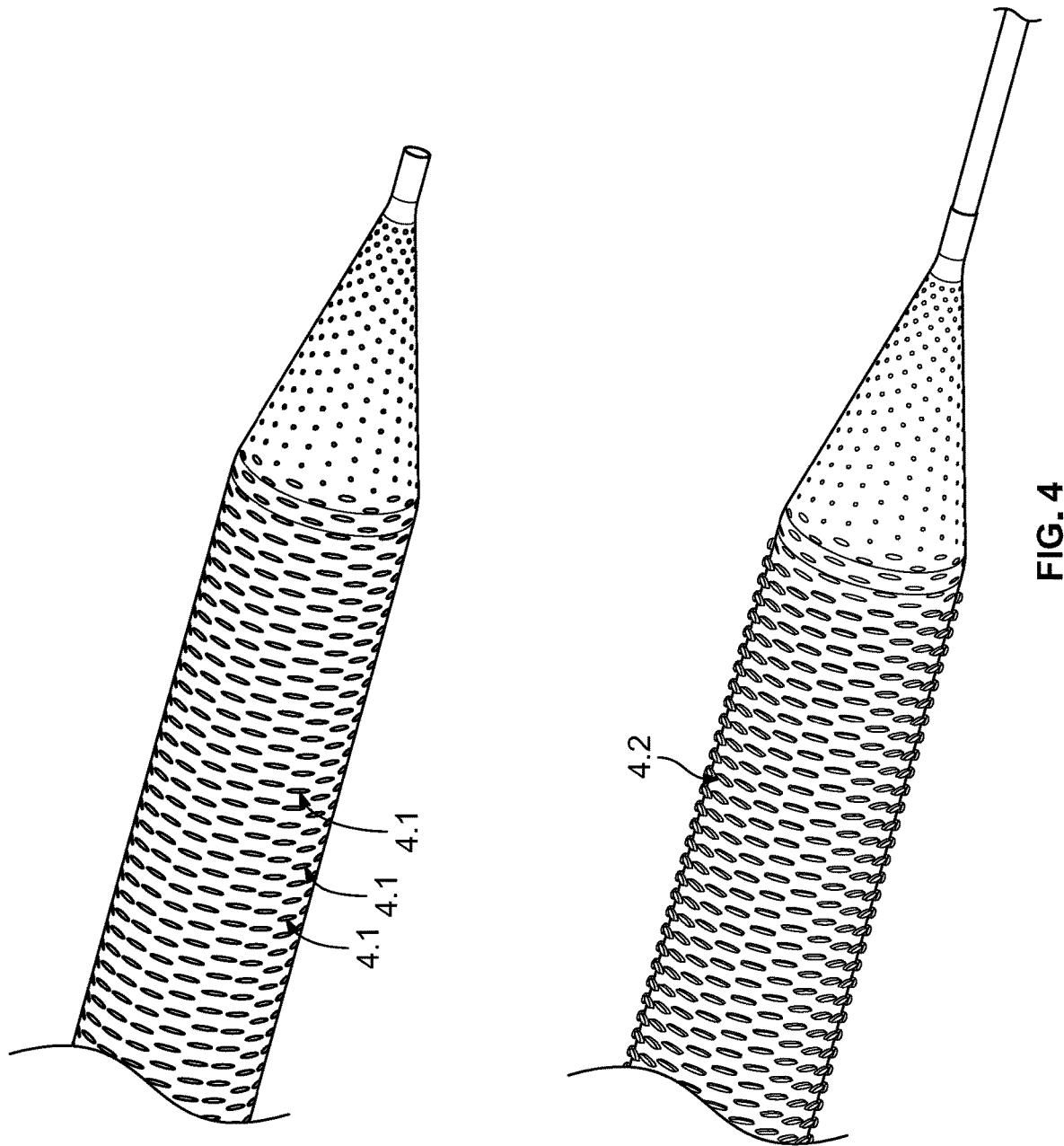
FIG. 4 shows the balloon in an expanded state with extrusion of the matrix.
Figure 5:
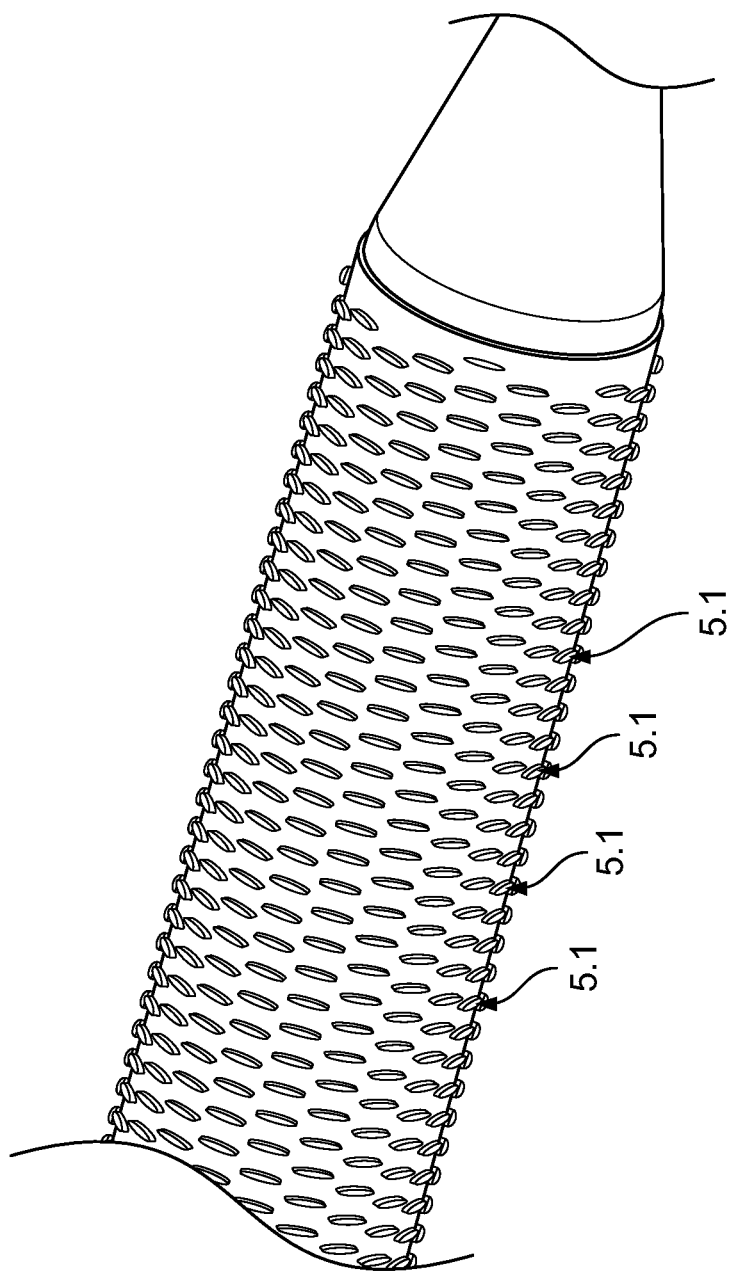
FIG. 5 shows a close-up view of FIG. 4.
Figure 6:
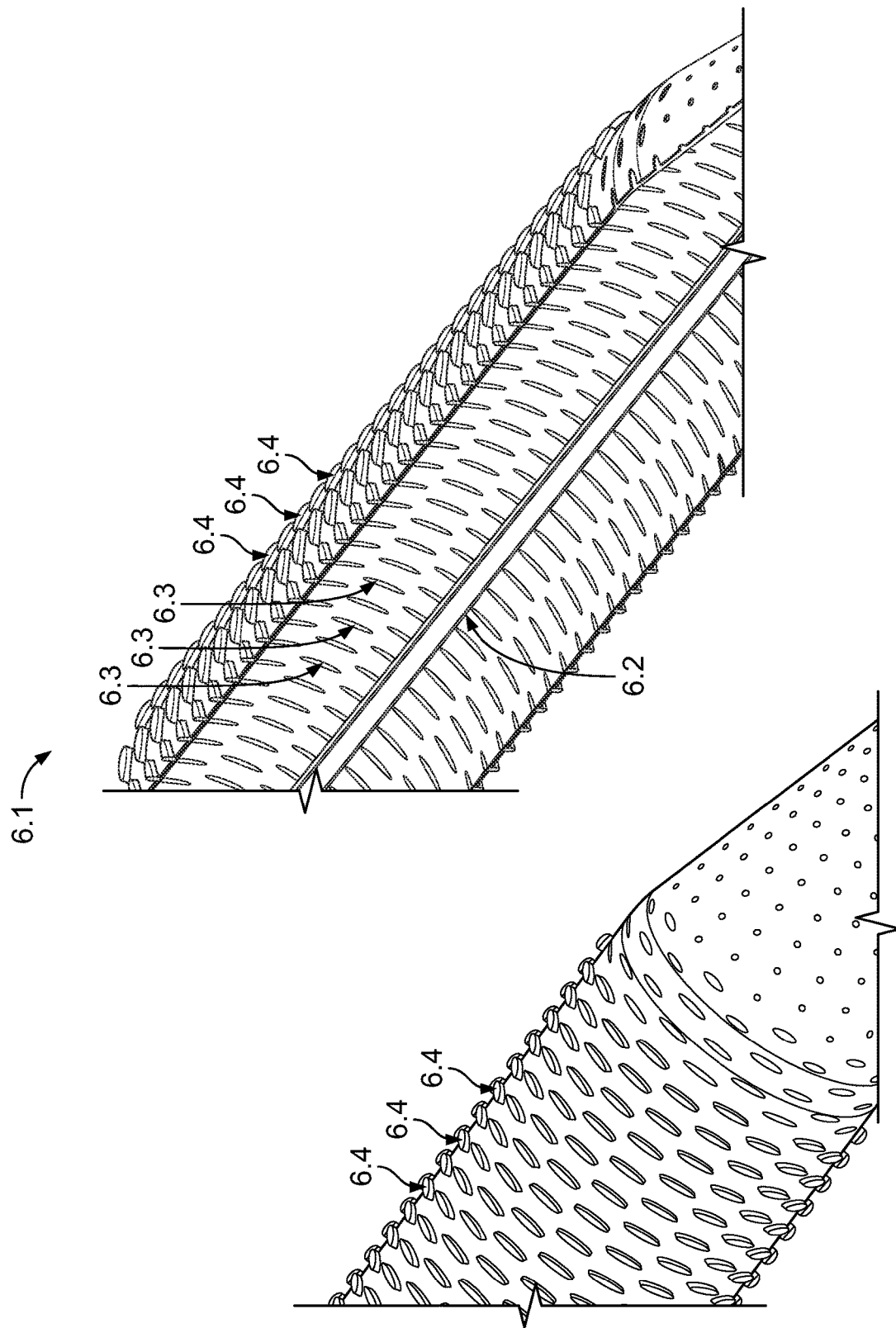
FIG. 6 shows a cross sectional view of the balloon in an expanded state with extrusion of the matrix/gel.

After expansion, the slits or pores in the expandable cover enlarge 4.1 (FIG. 4), allowing for extrusion of the biocompatible matrix into the body cavity 4.2. This extrusion is shown in a closeup view as 5.1 (FIG. 5). A cross section view of the balloon after expansion is shown in FIG. 6. The balloon 6.1 surrounds the guidewire 6.2. The enlarged slits/pores are shown as 6.3. Through these slits or pores, the biocompatible matrix 6.4 is extruded.

Figure 7:
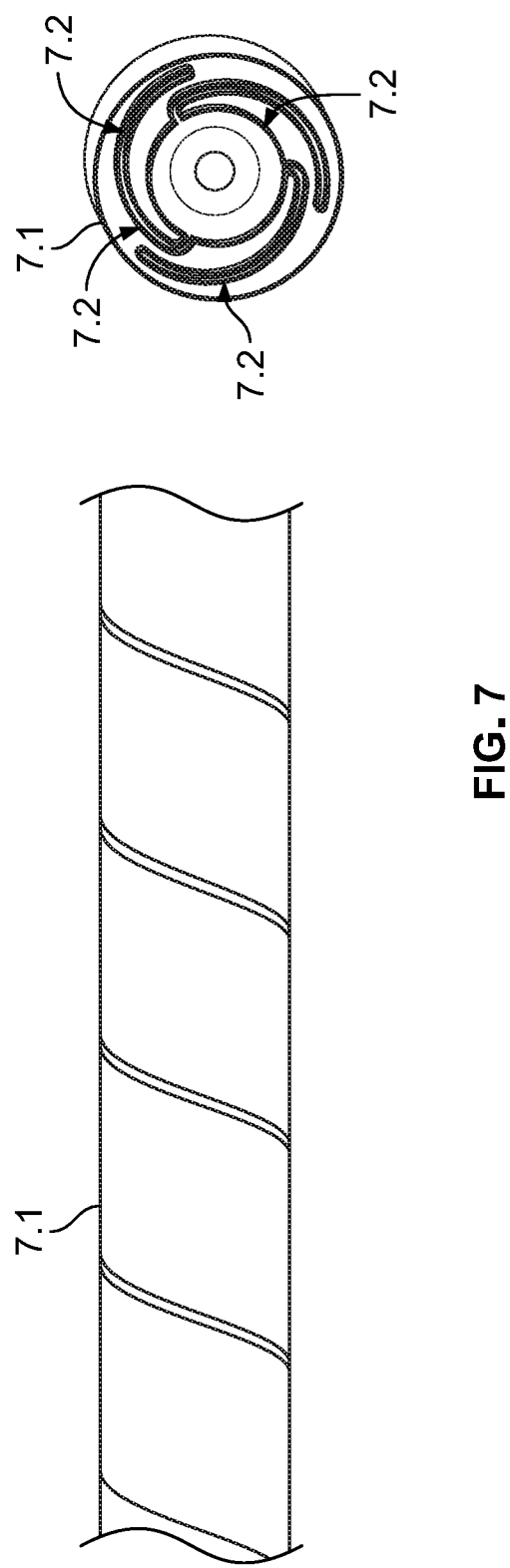
FIG. 7 shows the gel matrix forming a thin film wrapping around the balloon in a spiral configuration.
Figure 8:
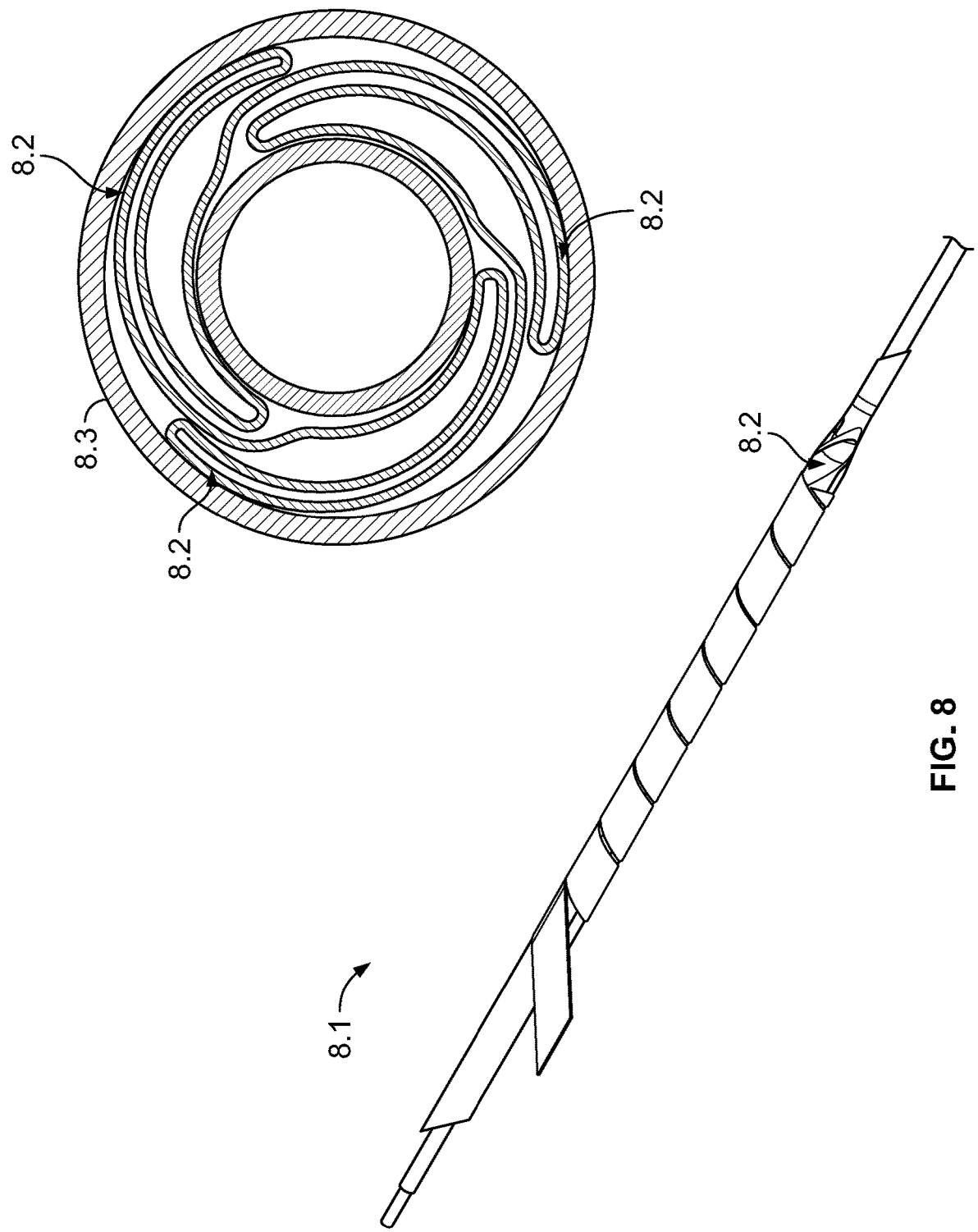
FIG. 8 shows a cross sectional view of the balloon in an unexpanded state enclosed by an expandable cover and a gel matrix formed in a wrap.
Figure 10A:
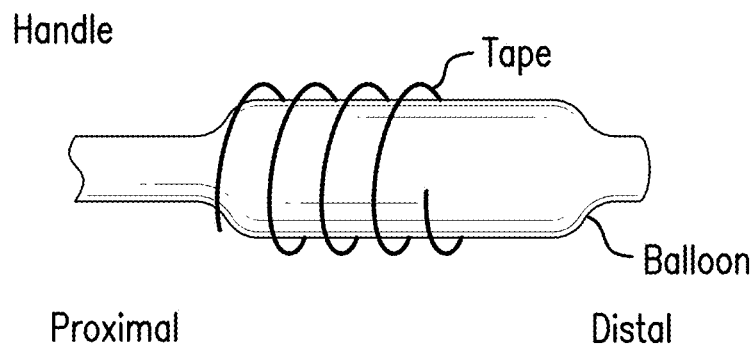
FIG. 10 illustrates the following possible configurations which should be considered non-limiting.
Figure 10B:
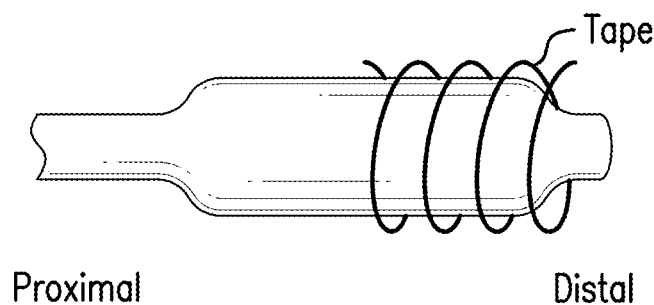
Figure 10C:
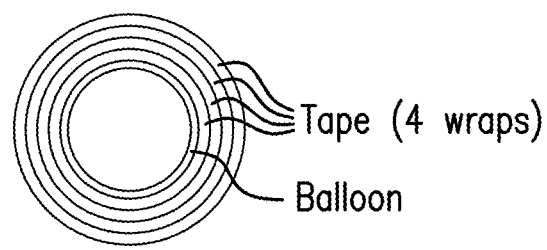
Figure 10D:
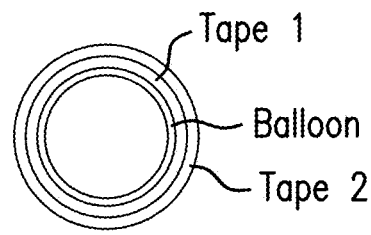
Figure 10E:
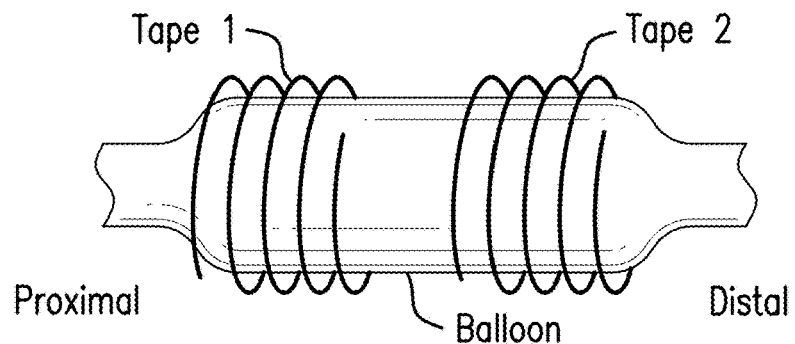
Figure 10F:
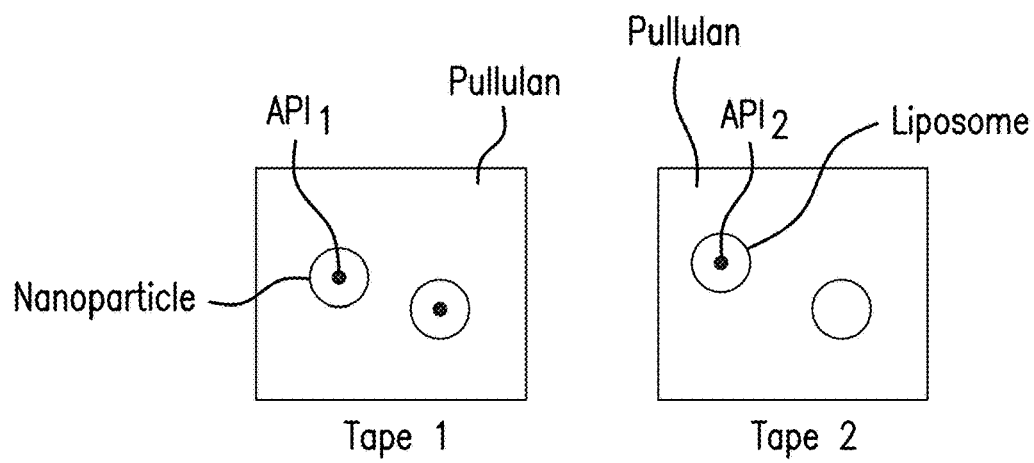
Figure 10G:
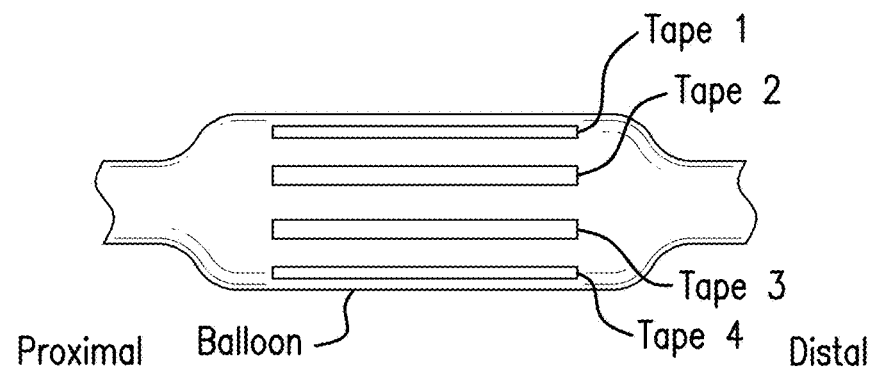

The biocompatible matrix can be formed from a spiral wrap 7.1 which surrounds, encloses or envelops the balloon 7.2 (FIG. 7). The wrapping with the expandable cover 8.3 of the pleated balloon 8.2 is shown in FIG. 8. The matrix, 9.1, wrapped spirally around the balloon 9.2 is enclosed with a expandable cover 9.3 which contains slits/pores 9.4 through which the matrix can be extruded (FIG. 9).

The subjects that can be treated using the medical device and methods of this invention are mammals, including, but not limited to, a human, horse, dog, cat, pig, rodent, monkey and the like.

The following are examples of the present invention and are not to be construed as limiting.

EXAMPLES

Example 1

Balloon Coatings (Paclitaxel)
(a) 90% paclitaxel/10% Mpeg-PLGA in chloroform—Paclitaxel was mixed in chloroform to a w/v concentration of 1.5% (15 mg/mL). The polymer was mixed in chloroform to a w/v concentration of 1.5% (15 mg/mL). The two solutions were then combined in the ratio of 90:10 respectively.
(b) 90% paclitaxel/10% Mpeg-PDLA in chloroform—Paclitaxel was mixed in chloroform to a w/v concentration of 1.5% (15 mg/mL). The polymer was mixed in chloroform to a w/v concentration of 1.5% (15 mg/mL). The two solutions were then combined in the ratio of 90:10 respectively.
(c) 90% paclitaxel/10% Iohexol in Distilled (DI) Water—Paclitaxel was mixed in acetone to a w/v concentration of 1.5% (15 mg/mL). Iohexol was mixed in deionized water to a w/v concentration of 1.5% (15 mg/mL). The two solutions were then combined in the ratios of 90:10 or 95:5 where applicable.
(d) 90% paclitaxel/10% Urea in DI Water—Paclitaxel was mixed in chloroform to a w/v concentration of 1.5% (15 mg/mL). The urea was mixed in de-ionized water to a w/v concentration of 1.5% (15 mg/mL). The two solutions were then combined in the ratio of 90:10 respectively.
(e) Coating of Balloons—3.0 mm×15 mm Sapphire® balloons were coated with the formulations listed above. Balloons were coated with target doses were 1 µg/mm², 2 µg/mm² and 3 µg/mm². Coated balloons were folded and sheathed immediately after coating.
(f) Solubility Studies—Glass slides will be coated with the various formulations. The coating will then be scraped off the glass slide into a crucible. The coating will then be weighed on the analytical balance (T/N 1160). Phosphate buffered saline (PBS) will be added to the pre-weighed coating to make a 10 mg/mL solution. The solution will then be vortexed for 3 minutes and filtered. 1 ml of solution will be extracted and filtered into a test tube using a 3 mL syringe and a 13 mm 0.45 µm PTFE filter. 1 ml of methanol will then be added to the filtered PBS and "vortexed" for 20 secs in order to dissolve any paclitaxel present. A 1 ml sample will then be analyzed for drug (paclitaxel) content.

Example 2

Balloon Coatings (Sirolimus)
(a) 90% sirolimus/10% Mpeg-PLGA in chloroform—Sirolimus will be mixed in chloroform to a w/v concentration of 1.5% (15 mg/mL). The polymer will be mixed in chloroform to a w/v concentration of 1.5% (15 mg/mL). The two solutions will then be combined in the ratio of 90:10 respectively.
(b) 90% sirolimus/10% Mpeg-PDLA in chloroform—Sirolimus will be mixed in chloroform to a w/v concentration of 1.5% (15 mg/mL). The polymer will be mixed in chloroform to a w/v concentration of 1.5% (15 mg/mL). The two solutions will then be combined in the ratio of 90:10 respectively.
(c) 90% sirolimus/10% Iohexol in Distilled (DI) Water—Sirolimus will be mixed in acetone to a w/v concentration of 1.5% (15 mg/mL). Iohexol will be mixed in deionized water to a w/v concentration of 1.5% (15 mg/mL). The two solutions will then be combined in the ratios of 90:10 or 95:5 where applicable.
(d) 90% sirolimus/10% Urea in DI Water—Sirolimus will be mixed in chloroform to a w/v concentration of 1.5% (15 mg/mL). The urea will be mixed in de-ionized water to a w/v concentration of 1.5% (15 mg/mL). The two solutions will then be combined in the ratio of 90:10 respectively.
(e) Coating of Balloons—3.0 mm×15 mm Sapphire® balloons will be coated with the formulations listed above. Balloons will be coated with target doses such as 1 µg/mm², 2 µg/mm² and 3 µg/mm². Coated balloons will be folded and sheathed immediately with the expandable cover after coating.
(f) Solubility Studies—Glass slides will be coated with the various formulations. The coating will then be scraped off the glass slide into a crucible. The coating will then be weighed on the analytical balance (T/N 1160). Phosphate buffered saline (PBS) will be added to the pre-weighed coating to make a 10 mg/mL solution. The solution will then be vortexed for 3 minutes and filtered. 1 ml of solution will be extracted and filtered into a test tube using a 3 mL syringe and a 13 mm 0.45 µm PTFE filter. 1 ml of methanol will be then added to the filtered PBS and vortexed for 20 secs in order to dissolve any sirolimus present. A 1 ml sample will then be analyzed for drug (sirolimus) content.

Example 3

Elution Profile (a) Elution Profile Kinetics—The coated balloon, with and without the expandable cover, will be placed in different 1 ml aliquots of PBS at 37° C. for a series of defined times, e.g., 30 seconds, 1, 2, 3, 4, 5, 10, 15, 30, 60 and 120 minutes in order to generate an elution profile over time. Aliquots of PBS will then be analyzed by high pressure liquid chromatography (HPLC) to establish sirolimus concentrations in solution at each time point. Calibration standards containing known amounts of sirolimus will be used to determine the amount of sirolimus eluted. The multiple peaks present for sirolimus (also present in the calibration standards) will be added to give the amount of sirolimus eluted at that time period (in absolute amount and as a cumulative amount eluted). High pressure liquid chromatography (HPLC) analysis will then performed using Waters HPLC system.

Example 4

Clinical Simulation Test (a) In-Vitro Mass Loss Test: The coated balloon with the expandable cover, prepared as in Example 2, will be weighed on a microbalance and then secured to a balloon catheter. A segment of optically clear TYGON® tubing will be filled with phosphate buffered saline (PBS) and immersed in a water bath at 37° C. in order to mimic physiological conditions of deployment in the body cavity of a subject. The coated balloon will be inserted into the tubing and the balloon will be inflated to at least about 25% to about 70% below the balloon's rated burst pressure (e.g., 5-15 atm) for 30 seconds, 1, 2, 3, 4, 5, 10, 15, 30, 60 or 120 minutes. The balloon will be deflated and then removed from the tubing. After drying, the balloon will be further dried and weighed on a microbalance. A comparison of the pre- and post-deployment weights indicates how much coating is freed, dissociated, and/or transferred from the balloon.
(b) In-Vitro Testing for Distal Flow: The coated balloon, prepared in Example 2, will be secured to a guidewire incorporating a porous filter of 100 µm pore size. A segment of TYGON® tubing will be filled with PBS and immersed in a water bath at 37° C. The coated balloon enclosed with the expandable cover will be inserted into the tubing. The flow of PBS through the TYGON tubing will be started, the distal filter will be deployed and the balloon will be inflated to at least 25% to about 70% below the balloon's rated burst pressure (e.g., 5-15 atm) for 30 seconds, 1, 2, 3, 4, 5, 10, 15, 30, 60 or 120 minutes. The balloon will be deflated and removed from the tubing. The filter will be deployed for 5 minutes after removal of the balloon and the flow of PBS will be halted, the tubing cut adjacent to the epoxy seal, the filter retracted and removed from the tubing. The content of the filter will be analyzed for the presence of sirolimus containing particles.

Example 5

Expanding Coated Balloon in Yucatan Minswine Arteries

A coated balloon will be prepared and then secured to a balloon catheter. Briefly, a balloon will be dip-coated in a coating composition (e.g., described in Example 1 or Example 2). The balloon will then be dried, folded, and secured to a balloon catheter.

A segment of resected coronary artery from Yucatan miniature swine will be positionally fixed and filled with PBS. The coronary artery will then be immersed in a water bath at 37° C. in order to mimic physiological conditions of deployment in a subject. The coated balloon will be inserted into the tubing and the balloon will be inflated to at least about 25% to about 70% below the balloon's rated burst pressure (e.g., 5-15 atm) for 30 seconds, 1, 2, 3, 4, 5, 10, 15, 30, 60 or 120 minutes. The balloon will be deflated and removed from the artery. The section of artery exposed to the deployed balloon will be cut away from the remainder of the artery section, placed into a tissue homogenizer and the homogenized material extracted with methylene chloride to make up 25 mL total volume of rinsings which will be collected in a flask for analysis. Analysis by HPLC as described above will be performed to determine the amount of sirolimus transferred from the balloon through the expandable cover to the coronary artery at each time point.

Sirolimus will also be extracted from the balloon by placing it in a 5 mL glass test tube containing 1 mL of methanol and vortexing for approximately 20 seconds. The balloon will be removed from the test tube and the contents of the test tube will be filtered into a 1 mL autosampler vial using a 3 mL syringe and 0.45 micron filter. Sirolimus concentrations will be assayed by HPLC.

Example 6

Optical Microscopy and Scanning Electron Microscopy (SEM) of the Balloon and Coating A coated balloon will be prepared using a coating composition, e.g., described in Example 1 or Example 2. The balloon will be covered with an expandable cover and immersed in PBS at 37° C. The coated balloon will be inserted into the TYGON® tubing as described above and the balloon will be inflated to at least about 25% to about 70% below the balloon's rated burst pressure (e.g., 5-15 atm) for about 30 seconds, 1, 2, 3, 4, 5, 10, 15, 30, 60 or 120 minutes. The balloon will be deflated and removed from the TYGON® tubing. SEM and Optical microscopy will be performed on the balloon and the expandable cover to determine physical changes occurred to the surfaces of the balloon and the expandable cover associated with transfer, disassociation, and displacement of the coating.

Example 7

In vivo Analysis of Active Pharmaceutical Agent at site of Application

A group of 10 New Zealand white rabbits will be prepared for a Seldinger procedure using a balloon coated with a formulation of sirolimus with total loading of sirolimus of approximately, 20-60 µg. The coated balloon will then enclosed by the expandable cover and then placed in the coronary artery. The covered and coated balloon catheter will be positioned with the assistance of fluoroscopy. Six animals will be subjected to the procedure using a coated balloon that does not have sirolimus in the coating. After deployment and removal of the balloon, 2 control animals will be sacrificed at 1 hour post deployment and serum and tissue samples will be collected. The 3 remaining control animals will be sacrificed at 56 days post deployment. During the course of the study, serum samples will be collected from control and drug-treated animals every five days. The drug treated animals, 3 each, will be sacrificed at 1 hour, 24 hours, 7 days, 14 days, 28 days, 42 days and 56 days post-deployment. The tissue and serum samples will be subjected to analysis for sirolimus concentration by HPLC as described above.

Example 8

The balloon is wrapped with a tape formed from Pullulan. Pullulan is a polysaccharide polymer consisting of maltotriose units, also known as α-1,4- ;α-1,6-glucan (see, https://pubchem.ncbi.nlm.nih.gov/compound/92024139, retrieved Jun. 30, 2017). The Pullulan may be mixed with an active pharmaceutical ingredient (API). The API may be suspended directly in the Pullulan. Alternatively, the API may be suspended in a particles such as: (i) Nanoparticulate suspensions; (ii) Solid lipid nanoparticles; (iii) PLGA; or (iv) LyoCells® (see, http://www.particlesciences.com/docs/technical_briefs/TB_2012_4-Cubic-Phase-Particles-in-Drug-Delivery.pdf, retrieved Jun. 30, 2017). These examples of partciles is non-limiting.

Only a portion of the balloon may be wrapped. As shown below, the Pullulan tape wraps the distal segment of the balloon (distal to the handle). Alternatively, the Pullulan tape wraps the proximal segment of the balloon (proximal to the handle). The balloon may be wrapped 1, 2, 3, 4, 5, 6, 7, 8, 9, 10 . . . n times with the Pullulan tape. The balloon may be wrapped with two or more (2, 3, 4, 5, 6, 7, 8, 9, 10 . . . n) different Pullulan tapes containing different APIs as well as different particles for suspension of the API. Various configurations of the wrapping are shown below.

FIG. 10 illustrates the following possible configurations which should be considered non-limiting.
(A) The balloon is shown with the tape wrapped around the proximal portion of the balloon.
(B) The balloon is shown with the tape wrapped around the distal portion of the balloon.
(C) The balloon is shown with four (4) wraps of the tape around the balloon.
(D) The balloon is shown with two different tapes, Tape 1 and Tape 2, wrapped around the balloon.
(E) The balloon is shown with two different tapes, Tape 1 and Tape 2, wrapped around the proximal, Tape 1, and distal, Tape 2, portions of the balloon.
(F) The Pullulan is shown with two different APIs, $API_1$ and $API_2$, suspended in a nanoparticle, $API_1$ and a liposome, $API_2$.
(G) The balloon is shown with four different Tapes, Tapes 1-4, aligned longitudinally along the balloon.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A medical device, comprising a balloon, a biocompatible matrix and an expandable polymer cover, wherein the balloon comprises a plurality of pleats when the balloon is not inflated, wherein the biocompatible matrix is disposed between the balloon and the expandable polymer cover, wherein the expandable polymer cover encloses the balloon and the biocompatible matrix, and wherein permeability of the expandable polymer cover when the balloon is inflated is greater than the permeability of the expandable polymer cover when the balloon is not inflated, wherein the biocompatible matrix comprises pullulan and a macrolide drug in a crystalline form, wherein the biocompatible matrix comprises a thin film having a thickness ranging from 3 µm to about 250 µm, and wherein the macrolide drug is released into an aqueous environment for at least 25 days after the balloon is inflated.

2. The medical device of claim 1, wherein the macrolide drug is encapsulated in a microsphere, liposome, nanoparticle, nanogel or mixtures thereof.

3. The medical device of claim 1, wherein the macrolide drug comprises everolimus, tacrolimus, zotarolimus, biolimus, rapamycin or mixtures thereof.

4. The medical device of claim 1, wherein the biocompatible matrix encloses the plurality of pleats.

5. The medical device of claim 4, wherein the biocompatible matrix is extruded through the expandable polymer cover after inflation of the balloon.

6. The medical device of claim 5, wherein the balloon is compliant, semi-compliant or non-compliant.

7. The medical device of claim 5, further comprising a plurality of holes, pores, slits, or combinations thereof in the expandable polymer cover.

8. The medical device of claim 7, wherein the biocompatible matrix is extruded through the plurality of holes in the expandable polymer cover when the balloon is inflated.

9. The medical device of claim 1, wherein the biocompatible matrix forms a tube enclosing the plurality of pleats.

10. The medical device of claim 1, wherein total surface load of the macrolide drug in the biocompatible matrix ranges from 1 µg/mm² to about 200 µg/mm².

11. The medical device of claim 10, wherein less than 10% (w/w) of the macrolide drug is released after incubation of the medical device for 10 minutes at 37 degrees Celsius in an aqueous solution, when the balloon is not inflated.

12. The medical device of claim 10, wherein greater than 75% (w/w) of the macrolide drug is released after incubation for 10 minutes at 37 degrees Celsius in an aqueous solution, when the balloon is inflated.

13. The medical device of claim 12, wherein the macrolide drug is released into the aqueous solution following zero-order kinetics.

14. The medical device of claim 1, wherein thickness of the expandable polymer cover ranges from 0.1 µm to about 300 µm.

15. The medical device of claim 1, wherein the biocompatible matrix further comprises dextran, alginate, amylose, amylopectin, carrageenan, carboxymethyl cellulose, gellan, guar gum, hydroxyethyl cellulose, hydroxypropyl cellulose, hydroxypropylmethyl cellulose, carboxymethyl cellulose, amylopectin, hyaluronic acid, xantan, xyloglucan, chitosan-based hydrogel, peptidoglycan, proteoglycans, glucose, polysaccharides, maltose, lactose, fructose, sucrose, galactose, glucosamine, galactosamine, muramic acid, glucuronate, gluconate, fucose, trehalose, polyvinyl alcohol, polyvinylpyrrolidone, polyethylene glycol, propylene glycol, polyoxyethylene derivatives, elastin, polyvinyl amine or poly(L-lysine), carboxymethyl cellulose (CMC), hydroxypropylmethyl cellulose (HPMC), amylopectin, hyaluronic acid or combinations thereof.

16. The medical device of claim 1, further comprising a bioadhesive.

17. The medical device of claim 1, wherein the biocompatible matrix is formed as a tape which is wrapped from 1 to 10 times around the pleats of the balloon.

18. The medical device of claim 17, further comprising at least two different tapes, wherein each tape comprises at least one macrolide drug.

19. The medical device of claim 18, wherein the at least one macrolide drug of the at least two different tapes comprises everolimus, tacrolimus, zotarolimus, biolimus, rapamycin or mixtures thereof.

20. The medical device of claim 1, wherein the expandable polymer cover is formed from high density, high molecular weight polyethylene (HDHMWPE), ultra-high molecular weight polyethylene (UHDHMWPE), poly(tetrafluoroethylene), poly(tetrafluoroethylene) (PTFE), ethylene vinyl acetate, latexes, urethanes, fluoropolymer, polyvinyl alcohol (PVA)-cross linked hydrogel, polysiloxanes, styrene-ethylene/butylene-styrene block copolymers, mixtures, copolymers or combinations thereof.

21. The medical device of claim 20, wherein the expandable polymer cover is made from ultra-high molecular weight polyethylene.

22. The medical device of claim 20, wherein the expandable polymer cover forms a tube which is sealed around the balloon.

23. The medical device of claim 1, wherein at least one marker band is positioned at either end of the balloon.

24. A medical device comprising, a balloon, a biocompatible matrix and an expandable polymer cover, wherein the balloon comprises a plurality of pleats when the balloon is not inflated, wherein the biocompatible matrix is disposed between the balloon and the expandable polymer cover, wherein the biocompatible matrix comprises at least one pharmaceutical agent encapsulated in a microsphere, liposome, nanoparticle or nanogel, wherein the at least one pharmaceutical agent is selected from the group consisting of everolimus, tacrolimus, sirolimus, zotarolimus, biolimus, rapamycin or mixtures thereof, and wherein the expandable polymer cover encloses the balloon, wherein permeability of the expandable polymer cover when the balloon is inflated is greater than the permeability of the expandable polymer cover when the balloon is not inflated, wherein the biocompatible matrix comprises pullulan, wherein the biocompatible matrix comprises a thin film having a thickness ranging from 3 µm to 250 µm, and wherein the at least one pharmaceutical agent is released into an aqueous environment for at least 25 days after the balloon is inflated.

25. The medical device of claim 24, the biocompatible matrix further comprises dextran, alginate, amylose, amylopectin, carrageenan, carboxymethyl cellulose, gellan, guar gum, hydroxyethyl cellulose, hydroxypropyl cellulose, hydroxypropylmethyl cellulose, carboxymethyl cellulose, amylopectin, hyaluronic acid, xantan, xyloglucan, chitosan-based hydrogel, peptidoglycan, proteoglycans, glucose, polysaccharides, maltose, lactose, fructose, sucrose, galactose, glucosamine, galactosamine, muramic acid, glucuronate, gluconate, fucose, trehalose, polyvinyl alcohol, polyvinylpyrrolidone, polyethylene glycol, propylene glycol, polyoxyethylene derivatives, elastin, polyvinyl amine or poly(L-lysine), carboxymethyl cellulose (CMC), hydroxypropylmethyl cellulose (HPMC), amylopectin, hyaluronic acid, or combinations thereof, a bioadhesive in the biocompatible matrix and the expandable cover is formed from high density, high molecular weight polyethylene (HDHMWPE), ultra-high molecular weight polyethylene (UHDHMWPE), poly(tetrafluoroethylene), poly(tetrafluoroethylene) (PTFE), ethylene vinyl acetate, latexes, urethanes, fluoropolymer, polyvinyl alcohol (PVA)-cross linked hydrogel, polysiloxanes, styrene-ethylene/butylene-styrene block copolymers, mixtures, copolymers or combinations thereof.

26. The medical device of claim 25, wherein the balloon is compliant, semi-compliant or non-compliant.

* * * * *